US009226772B2

(12) United States Patent
Fox

(10) Patent No.: US 9,226,772 B2
(45) Date of Patent: Jan. 5, 2016

(54) SURGICAL DEVICE

(75) Inventor: William D. Fox, New Richmond, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 968 days.

(21) Appl. No.: 12/363,137

(22) Filed: Jan. 30, 2009

(65) Prior Publication Data

US 2010/0198149 A1 Aug. 5, 2010

(51) Int. Cl.

| | |
|---|---|
| ***A61B 17/34*** | (2006.01) |
| *A61B 17/00* | (2006.01) |
| *A61B 17/06* | (2006.01) |
| *A61B 17/22* | (2006.01) |
| *A61B 17/30* | (2006.01) |
| *A61M 29/02* | (2006.01) |

(52) U.S. Cl.

CPC ..... *A61B 17/3478* (2013.01); *A61B 2017/0034* (2013.01); *A61B 2017/00278* (2013.01); *A61B 2017/06076* (2013.01); *A61B 2017/22061* (2013.01); *A61B 2017/306* (2013.01); *A61B 2017/349* (2013.01); *A61B 2017/3484* (2013.01); *A61M 29/02* (2013.01)

(58) Field of Classification Search

CPC ..................... A61B 17/3478; A61B 2017/349; A61B 2017/00278; A61B 2017/06076; A61B 2017/0034; A61B 2017/3484; A61B 2017/306; A61B 2017/22061; A61M 29/02

USPC ......................... 606/185, 194, 180, 191–192; 604/99.01, 164.01, 509–510, 274, 206; 600/104

See application file for complete search history.

(56) References Cited

U.S. PATENT DOCUMENTS

| | | | |
|---|---|---|---|
| 645,576 | A | 3/1900 | Telsa |
| 649,621 | A | 5/1900 | Tesla |
| 787,412 | A | 4/1905 | Tesla |
| 1,127,948 | A | 2/1915 | Wappler |
| 1,482,653 | A | 2/1924 | Lilly |
| 1,625,602 | A | 4/1927 | Gould et al. |
| 2,028,635 | A | 1/1936 | Wappler |
| 2,031,682 | A | 2/1936 | Wappler et al. |
| 2,113,246 | A | 4/1938 | Wappler |
| 2,155,365 | A | 4/1939 | Rankin |
| 2,191,858 | A | 2/1940 | Moore |
| 2,196,620 | A | 4/1940 | Attarian |

(Continued)

FOREIGN PATENT DOCUMENTS

| | | | |
|---|---|---|---|
| AU | 666310 | B2 | 2/1996 |
| DE | 3008120 | A1 | 9/1980 |

(Continued)

OTHER PUBLICATIONS

Michael S. Kavic, M.D., "Natural Orifice Translumenal Endoscopic Surgery: "NOTES"", JSLS, vol. 10, pp. 133-134 (2006).

(Continued)

*Primary Examiner* — Tuan V Nguyen
*Assistant Examiner* — Tin Nguyen

(57) ABSTRACT

A surgical device comprises a guide tube having a proximal end, a distal end, and an inside diameter. A needle has a proximal end and a distal end. The needle comprises a longitudinal portion having a diameter suitable to be slidably received within the inside diameter of the guide tube. The needle comprises a helical element disposed at the distal end of the needle.

19 Claims, 17 Drawing Sheets

(56) References Cited

U.S. PATENT DOCUMENTS 2,388,137 A 10/1945 Graumlich
2,493,108 A 1/1950 Casey, Jr.
2,504,152 A 4/1950 Riker et al.
2,938,382 A 5/1960 De Graaf
2,952,206 A 9/1960 Becksted
3,069,195 A 12/1962 Buck
3,170,471 A 2/1965 Schnitzer
3,435,824 A 4/1969 Gamponia
3,470,876 A 10/1969 Barchilon
3,595,239 A 7/1971 Petersen
3,669,487 A 6/1972 Roberts et al.
3,746,881 A 7/1973 Fitch et al.
3,799,672 A 3/1974 Vurek
3,854,473 A 12/1974 Matsuo
3,946,740 A 3/1976 Bassett
3,948,251 A 4/1976 Hosono
3,994,301 A 11/1976 Agris
4,011,872 A 3/1977 Komiya
4,012,812 A 3/1977 Black
4,085,743 A 4/1978 Yoon
4,164,225 A 8/1979 Johnson et al.
4,178,920 A 12/1979 Cawood, Jr. et al.
4,207,873 A 6/1980 Kruy
4,235,238 A 11/1980 Ogiu et al.
4,258,716 A 3/1981 Sutherland
4,269,174 A 5/1981 Adair
4,278,077 A 7/1981 Mizumoto
4,285,344 A 8/1981 Marshall
4,311,143 A 1/1982 Komiya
4,329,980 A 5/1982 Terada
4,396,021 A 8/1983 Baumgartner
4,406,656 A 9/1983 Hattler et al.
4,452,246 A 6/1984 Bader et al.
4,461,281 A 7/1984 Carson
4,491,132 A 1/1985 Aikins
4,527,331 A 7/1985 Lasner et al.
4,527,564 A 7/1985 Eguchi et al.
4,538,594 A 9/1985 Boebel et al.
D281,104 S 10/1985 Davison
4,569,347 A 2/1986 Frisbie
4,580,551 A 4/1986 Siegmund et al.
4,646,722 A 3/1987 Silverstein et al.
4,653,476 A 3/1987 Bonnet
4,655,219 A 4/1987 Petruzzi
4,669,470 A 6/1987 Brandfield
4,671,477 A 6/1987 Cullen
4,685,447 A 8/1987 Iversen et al.
4,711,240 A 12/1987 Goldwasser et al.
4,712,545 A 12/1987 Honkanen
4,721,116 A 1/1988 Schintgen et al.
4,733,662 A 3/1988 DeSatnick et al.
D295,894 S 5/1988 Sharkany et al.
4,763,669 A 8/1988 Jaeger
4,770,188 A 9/1988 Chikama
4,815,450 A 3/1989 Patel
4,823,794 A 4/1989 Pierce
4,829,999 A 5/1989 Auth
4,867,140 A 9/1989 Hovis et al.
4,873,979 A 10/1989 Hanna
4,880,015 A 11/1989 Nierman
4,911,148 A 3/1990 Sosnowski et al.
4,926,860 A 5/1990 Stice et al.
4,938,214 A 7/1990 Specht et al.
4,950,273 A 8/1990 Briggs
4,950,285 A 8/1990 Wilk
4,960,133 A 10/1990 Hewson
4,977,887 A 12/1990 Gouda
4,979,950 A 12/1990 Transue et al.
4,984,581 A 1/1991 Stice
5,007,917 A 4/1991 Evans
5,010,876 A 4/1991 Henley et al.
5,020,514 A 6/1991 Heckele
5,020,535 A 6/1991 Parker et al.
5,025,778 A 6/1991 Silverstein et al.
5,033,169 A 7/1991 Bindon
5,037,433 A 8/1991 Wilk et al.
5,041,129 A 8/1991 Hayhurst et al.
5,046,513 A 9/1991 Gatturna et al.
5,050,585 A 9/1991 Takahashi
5,052,372 A 10/1991 Shapiro
5,065,516 A 11/1991 Dulebohn
5,066,295 A 11/1991 Kozak et al.
5,123,913 A 6/1992 Wilk et al.
5,123,914 A 6/1992 Cope
5,133,727 A 7/1992 Bales et al.
5,147,374 A 9/1992 Fernandez
5,174,300 A 12/1992 Bales et al.
5,176,126 A 1/1993 Chikama
5,190,050 A 3/1993 Nitzsche
5,190,555 A 3/1993 Wetter et al.
5,192,284 A 3/1993 Pleatman
5,201,752 A 4/1993 Brown et al.
5,201,908 A 4/1993 Jones
5,203,785 A 4/1993 Slater
5,203,787 A 4/1993 Noblitt et al.
5,209,747 A 5/1993 Knoepfler
5,217,003 A 6/1993 Wilk
5,217,453 A 6/1993 Wilk
5,219,357 A 6/1993 Honkanen et al.
5,219,358 A 6/1993 Bendel et al.
5,222,362 A 6/1993 Maus et al.
5,222,965 A 6/1993 Haughton
5,234,437 A * 8/1993 Sepetka ........................ 606/108
5,234,453 A 8/1993 Smith et al.
5,235,964 A 8/1993 Abenaim
5,242,456 A 9/1993 Nash et al.
5,246,424 A 9/1993 Wilk
5,259,366 A 11/1993 Reydel et al.
5,263,958 A 11/1993 deGuillebon et al.
5,273,524 A 12/1993 Fox et al.
5,275,607 A 1/1994 Lo et al.
5,284,128 A 2/1994 Hart
5,284,162 A 2/1994 Wilk
5,287,845 A 2/1994 Faul et al.
5,290,299 A 3/1994 Fain et al.
5,290,302 A 3/1994 Pericic
5,295,977 A 3/1994 Cohen et al.
5,297,536 A 3/1994 Wilk
5,301,061 A 4/1994 Nakada et al.
5,312,333 A 5/1994 Churinetz et al.
5,312,351 A 5/1994 Gerrone
5,312,416 A 5/1994 Spaeth et al.
5,312,423 A 5/1994 Rosenbluth et al.
5,318,589 A 6/1994 Lichtman
5,320,636 A 6/1994 Slater
5,325,845 A 7/1994 Adair
5,330,471 A 7/1994 Eggers
5,330,486 A 7/1994 Wilk
5,330,488 A 7/1994 Goldrath
5,330,496 A 7/1994 Alferness
5,330,502 A 7/1994 Hassler et al.
5,331,971 A 7/1994 Bales et al.
5,334,198 A 8/1994 Hart et al.
5,344,428 A 9/1994 Griffiths
5,350,391 A 9/1994 Iacovelli
5,352,184 A 10/1994 Goldberg et al.
5,352,222 A 10/1994 Rydell
5,354,302 A 10/1994 Ko
5,354,311 A 10/1994 Kambin et al.
5,356,408 A 10/1994 Rydell
5,364,408 A 11/1994 Gordon
5,364,410 A 11/1994 Failla et al.
5,366,466 A 11/1994 Christian et al.
5,366,467 A 11/1994 Lynch et al.
5,368,605 A 11/1994 Miller, Jr.
5,370,647 A 12/1994 Graber et al.
5,370,679 A 12/1994 Atlee, III
5,374,273 A 12/1994 Nakao et al.
5,374,275 A 12/1994 Bradley et al.
5,374,277 A 12/1994 Hassler
5,377,695 A 1/1995 An Haack
5,383,877 A 1/1995 Clarke
5,383,888 A 1/1995 Zvenyatsky et al.
5,386,817 A 2/1995 Jones

(56) References Cited

U.S. PATENT DOCUMENTS 5,391,174 A 2/1995 Weston
5,392,789 A 2/1995 Slater et al.
5,395,386 A 3/1995 Slater
5,401,248 A 3/1995 Bencini
5,403,328 A 4/1995 Shallman
5,403,342 A 4/1995 Tovey et al.
5,403,348 A 4/1995 Bonutti
5,405,073 A 4/1995 Porter
5,405,359 A 4/1995 Pierce
5,409,478 A 4/1995 Gerry et al.
5,417,699 A 5/1995 Klein et al.
5,423,821 A 6/1995 Pasque
5,433,721 A 7/1995 Hooven et al.
5,439,471 A 8/1995 Kerr
5,439,478 A 8/1995 Palmer
5,441,059 A 8/1995 Dannan
5,441,499 A 8/1995 Fritzsch
5,443,463 A 8/1995 Stern et al.
5,445,638 A 8/1995 Rydell et al.
5,449,021 A 9/1995 Chikama
5,456,667 A 10/1995 Ham et al.
5,456,684 A 10/1995 Schmidt et al.
5,458,131 A 10/1995 Wilk
5,458,583 A 10/1995 McNeely et al.
5,460,168 A 10/1995 Masubuchi et al.
5,460,629 A 10/1995 Shlain et al.
5,462,561 A 10/1995 Voda
5,465,731 A 11/1995 Bell et al.
5,467,763 A 11/1995 McMahon et al.
5,468,250 A 11/1995 Paraschac et al.
5,470,308 A 11/1995 Edwards et al.
5,470,320 A 11/1995 Tiefenbrun et al.
5,478,347 A 12/1995 Aranyi
5,480,404 A 1/1996 Kammerer et al.
5,482,054 A 1/1996 Slater et al.
5,484,451 A 1/1996 Akopov et al.
5,489,256 A 2/1996 Adair
5,496,347 A 3/1996 Hashiguchi et al.
5,499,990 A 3/1996 Schülken et al.
5,499,992 A 3/1996 Meade et al.
5,501,692 A 3/1996 Riza
5,503,616 A 4/1996 Jones
5,505,686 A 4/1996 Willis et al.
5,507,755 A 4/1996 Gresl et al.
5,511,564 A 4/1996 Wilk
5,514,157 A 5/1996 Nicholas et al.
5,522,829 A 6/1996 Michalos
5,522,830 A 6/1996 Aranyi
5,527,321 A 6/1996 Hinchliffe
5,536,248 A 7/1996 Weaver et al.
5,540,648 A 7/1996 Yoon
5,554,151 A 9/1996 Hinchliffe
5,555,883 A 9/1996 Avitall
5,558,133 A 9/1996 Bortoli et al.
5,562,693 A 10/1996 Devlin et al.
5,569,243 A 10/1996 Kortenbach et al.
5,569,298 A 10/1996 Schnell
5,573,540 A 11/1996 Yoon
5,578,030 A 11/1996 Levin
5,582,611 A 12/1996 Tsuruta et al.
5,582,617 A 12/1996 Klieman et al.
5,584,845 A 12/1996 Hart
5,591,179 A 1/1997 Edelstein
5,593,420 A 1/1997 Eubanks, Jr et al.
5,595,562 A 1/1997 Grier
5,597,378 A 1/1997 Jervis
5,601,573 A 2/1997 Fogelberg et al.
5,601,588 A 2/1997 Tonomura et al.
5,604,531 A 2/1997 Iddan et al.
5,607,389 A 3/1997 Edwards et al.
5,607,450 A 3/1997 Zvenyatsky et al.
5,613,975 A 3/1997 Christy
5,618,303 A 4/1997 Marlow et al.
5,620,415 A 4/1997 Lucey et al.
5,624,399 A 4/1997 Ackerman
5,624,431 A 4/1997 Gerry et al.
5,626,578 A 5/1997 Tihon
5,628,732 A 5/1997 Antoon, Jr. et al.
5,630,782 A 5/1997 Adair
5,643,283 A 7/1997 Younker
5,643,292 A 7/1997 Hart
5,643,294 A 7/1997 Tovey et al.
5,644,798 A 7/1997 Shah
5,645,083 A 7/1997 Essig et al.
5,645,565 A 7/1997 Rudd et al.
5,649,372 A 7/1997 Souza
5,653,677 A 8/1997 Okada et al.
5,653,690 A 8/1997 Booth et al.
5,653,722 A 8/1997 Kieturakis
5,662,663 A 9/1997 Shallman
5,669,875 A 9/1997 van Eerdenburg
5,681,324 A 10/1997 Kammerer et al.
5,681,330 A 10/1997 Hughett et al.
5,685,820 A 11/1997 Riek et al.
5,690,656 A 11/1997 Cope et al.
5,690,660 A 11/1997 Kauker et al.
5,695,448 A 12/1997 Kimura et al.
5,695,505 A 12/1997 Yoon
5,695,511 A 12/1997 Cano et al.
5,700,275 A 12/1997 Bell et al.
5,702,438 A 12/1997 Avitall
5,704,892 A 1/1998 Adair
5,709,708 A 1/1998 Thal
5,716,326 A 2/1998 Dannan
5,730,740 A 3/1998 Wales et al.
5,735,849 A 4/1998 Baden et al.
5,741,234 A 4/1998 Aboul-Hosn
5,741,278 A 4/1998 Stevens
5,741,285 A 4/1998 McBrayer et al.
5,746,759 A 5/1998 Meade et al.
5,749,881 A 5/1998 Sackier et al.
5,749,889 A 5/1998 Bacich et al.
5,752,951 A 5/1998 Yanik
5,755,731 A 5/1998 Grinberg
5,766,167 A 6/1998 Eggers et al.
5,766,170 A 6/1998 Eggers
5,766,205 A 6/1998 Zvenyatsky et al.
5,769,849 A 6/1998 Eggers
5,779,701 A 7/1998 McBrayer et al.
5,779,716 A 7/1998 Cano et al.
5,779,727 A 7/1998 Orejola
5,782,859 A 7/1998 Nicholas et al.
5,782,866 A 7/1998 Wenstrom, Jr.
5,791,022 A 8/1998 Bohman
5,792,113 A 8/1998 Kramer et al.
5,792,153 A 8/1998 Swain et al.
5,792,165 A 8/1998 Klieman et al.
5,797,835 A 8/1998 Green
5,797,928 A 8/1998 Kogasaka
5,797,939 A 8/1998 Yoon
5,797,941 A 8/1998 Schulze et al.
5,797,960 A * 8/1998 Stevens et al. ................ 606/213
5,803,903 A 9/1998 Athas et al.
5,808,665 A 9/1998 Green
5,810,806 A 9/1998 Ritchart et al.
5,810,849 A 9/1998 Kontos
5,810,865 A 9/1998 Koscher et al.
5,810,876 A 9/1998 Kelleher
5,810,877 A 9/1998 Roth et al.
5,813,976 A 9/1998 Filipi et al.
5,814,058 A 9/1998 Carlson et al.
5,817,061 A 10/1998 Goodwin et al.
5,817,107 A 10/1998 Schaller
5,817,119 A 10/1998 Klieman et al.
5,819,736 A 10/1998 Avny et al.
5,824,071 A 10/1998 Nelson et al.
5,827,281 A 10/1998 Levin
5,827,299 A 10/1998 Thomason et al.
5,830,231 A 11/1998 Geiges, Jr.
5,833,700 A 11/1998 Fogelberg et al.
5,833,703 A 11/1998 Manushakian
5,843,017 A 12/1998 Yoon
5,843,121 A 12/1998 Yoon
5,849,022 A 12/1998 Sakashita et al.

(56) References Cited

U.S. PATENT DOCUMENTS 5,853,374 A 12/1998 Hart et al.
5,855,585 A 1/1999 Kontos
5,860,913 A 1/1999 Yamaya et al.
5,860,995 A 1/1999 Berkelaar
5,868,762 A 2/1999 Cragg et al.
5,876,411 A 3/1999 Kontos
5,882,331 A 3/1999 Sasaki
5,882,344 A 3/1999 Stouder, Jr.
5,893,846 A 4/1999 Bales et al.
5,893,874 A 4/1999 Bourque et al.
5,893,875 A 4/1999 O'Connor et al.
5,899,919 A 5/1999 Eubanks, Jr. et al.
5,902,254 A 5/1999 Magram
5,904,702 A 5/1999 Ek et al.
5,908,420 A 6/1999 Parins et al.
5,911,737 A 6/1999 Lee et al.
5,916,147 A 6/1999 Boury
5,921,993 A 7/1999 Yoon
5,921,997 A 7/1999 Fogelberg et al.
5,922,008 A 7/1999 Gimpelson
5,925,052 A 7/1999 Simmons
5,928,255 A 7/1999 Meade et al.
5,928,266 A 7/1999 Kontos
5,936,536 A 8/1999 Morris
5,944,718 A 8/1999 Austin et al.
5,951,549 A 9/1999 Richardson et al.
5,954,720 A 9/1999 Wilson et al.
5,954,731 A 9/1999 Yoon
5,957,943 A 9/1999 Vaitekunas
5,957,953 A 9/1999 DiPoto et al.
5,971,995 A 10/1999 Rousseau
5,976,074 A 11/1999 Moriyama
5,976,075 A 11/1999 Beane et al.
5,976,130 A 11/1999 McBrayer et al.
5,976,131 A 11/1999 Guglielmi et al.
5,980,539 A 11/1999 Kontos
5,980,556 A 11/1999 Giordano et al.
5,984,938 A 11/1999 Yoon
5,984,939 A 11/1999 Yoon
5,989,182 A 11/1999 Hori et al.
5,993,447 A 11/1999 Blewett et al.
5,997,555 A 12/1999 Kontos
6,001,120 A 12/1999 Levin
6,004,269 A 12/1999 Crowley et al.
6,004,330 A 12/1999 Middleman et al.
6,007,566 A 12/1999 Wenstrom, Jr.
6,010,515 A 1/2000 Swain et al.
6,012,494 A 1/2000 Balazs
6,017,356 A 1/2000 Frederick et al.
6,019,770 A 2/2000 Christoudias
6,024,708 A 2/2000 Bales et al.
6,024,747 A 2/2000 Kontos
6,027,522 A 2/2000 Palmer
6,030,365 A 2/2000 Laufer
6,030,634 A 2/2000 Wu et al.
6,033,399 A 3/2000 Gines
6,036,685 A 3/2000 Mueller
6,053,927 A 4/2000 Hamas
6,066,160 A 5/2000 Colvin et al.
6,068,603 A 5/2000 Suzuki
6,068,629 A 5/2000 Haissaguerre et al.
6,071,233 A 6/2000 Ishikawa et al.
6,074,408 A 6/2000 Freeman
6,086,530 A 7/2000 Mack
6,090,108 A 7/2000 McBrayer et al.
6,096,046 A 8/2000 Weiss
6,102,926 A 8/2000 Tartaglia et al.
6,106,473 A 8/2000 Violante et al.
6,109,852 A 8/2000 Shahinpoor et al.
6,110,154 A 8/2000 Shimomura et al.
6,110,183 A 8/2000 Cope
6,113,593 A 9/2000 Tu et al.
6,117,144 A 9/2000 Nobles et al.
6,117,158 A 9/2000 Measamer et al.
6,139,555 A 10/2000 Hart et al.
6,146,391 A 11/2000 Cigaina
6,148,222 A 11/2000 Ramsey, III
6,149,653 A 11/2000 Deslauriers
6,149,662 A 11/2000 Pugliesi et al.
6,159,200 A 12/2000 Verdura et al.
6,165,184 A 12/2000 Verdura et al.
6,168,570 B1 1/2001 Ferrera
6,168,605 B1 1/2001 Measamer et al.
6,170,130 B1 1/2001 Hamilton et al.
6,179,776 B1 1/2001 Adams et al.
6,179,837 B1 1/2001 Hooven
6,183,420 B1 2/2001 Douk et al.
6,190,353 B1 2/2001 Makower et al.
6,190,384 B1 2/2001 Ouchi
6,190,399 B1 2/2001 Palmer et al.
6,203,533 B1 3/2001 Ouchi
6,206,872 B1 3/2001 Lafond et al.
6,206,877 B1 3/2001 Kese et al.
6,214,007 B1 4/2001 Anderson
6,228,096 B1 5/2001 Marchand
6,234,958 B1 5/2001 Snoke et al.
6,245,079 B1 6/2001 Nobles et al.
6,246,914 B1 6/2001 de la Rama et al.
6,258,064 B1 7/2001 Smith et al.
6,261,242 B1 7/2001 Roberts et al.
6,264,664 B1 7/2001 Avellanet
6,270,497 B1 8/2001 Sekino et al.
6,270,505 B1 8/2001 Yoshida et al.
6,277,136 B1 8/2001 Bonutti
6,283,963 B1 9/2001 Regula
6,293,909 B1 9/2001 Chu et al.
6,293,952 B1 9/2001 Brosens et al.
6,296,630 B1 10/2001 Altman et al.
6,322,578 B1 11/2001 Houle et al.
6,326,177 B1 12/2001 Schoenbach et al.
6,328,730 B1 12/2001 Harkrider, Jr.
6,350,267 B1 2/2002 Stefanchik
6,350,278 B1 2/2002 Lenker et al.
6,352,503 B1 3/2002 Matsui et al.
6,352,543 B1 3/2002 Cole
6,355,035 B1 3/2002 Manushakian
6,361,534 B1 3/2002 Chen et al.
6,371,956 B1 4/2002 Wilson et al.
6,379,366 B1 4/2002 Fleischman et al.
6,383,195 B1 5/2002 Richard
6,383,197 B1 5/2002 Conlon et al.
6,391,029 B1 5/2002 Hooven et al.
6,402,735 B1 6/2002 Langevin
6,406,440 B1 6/2002 Stefanchik
6,409,727 B1 6/2002 Bales et al.
6,409,733 B1 6/2002 Conlon et al.
6,427,089 B1 7/2002 Knowlton
6,431,500 B1 8/2002 Jacobs et al.
6,443,970 B1 9/2002 Schulze et al.
6,443,988 B2 9/2002 Felt et al.
6,447,511 B1 9/2002 Slater
6,447,523 B1 9/2002 Middleman et al.
6,454,783 B1 9/2002 Piskun
6,454,785 B2 9/2002 De Hoyos Garza
6,458,076 B1 10/2002 Pruitt
6,464,701 B1 10/2002 Hooven et al.
6,464,702 B2 10/2002 Schulze et al.
6,475,104 B1 11/2002 Lutz et al.
6,485,411 B1 11/2002 Konstorum et al.
6,489,745 B1 12/2002 Koreis
6,491,626 B1 12/2002 Stone et al.
6,491,627 B1 12/2002 Komi
6,491,691 B1 12/2002 Morley et al.
6,493,590 B1 12/2002 Wessman et al.
6,494,893 B2 12/2002 Dubrul et al.
6,500,176 B1 12/2002 Truckai et al.
6,503,192 B1 1/2003 Ouchi
6,506,190 B1 1/2003 Walshe
6,508,827 B1 1/2003 Manhes
6,514,239 B2 2/2003 Shimmura et al.
6,520,954 B2 2/2003 Ouchi
6,543,456 B1 4/2003 Freeman
6,551,270 B1 4/2003 Bimbo et al.
6,554,829 B2 4/2003 Schulze et al.

(56) References Cited

U.S. PATENT DOCUMENTS 6,558,384 B2 5/2003 Mayenberger
6,562,035 B1 5/2003 Levin
6,562,052 B2 5/2003 Nobles et al.
6,569,159 B1 5/2003 Edwards et al.
6,572,629 B2 6/2003 Kalloo et al.
6,572,635 B1 6/2003 Bonutti
6,575,988 B2 6/2003 Rousseau
6,579,311 B1 6/2003 Makower
6,585,642 B2 7/2003 Christopher
6,585,717 B1 7/2003 Wittenberger et al.
6,587,750 B2 7/2003 Gerbi et al.
6,592,559 B1 7/2003 Pakter et al.
6,592,603 B2 7/2003 Lasner
6,602,262 B2 8/2003 Griego et al.
6,605,105 B1 8/2003 Cuschieri et al.
6,610,072 B1 8/2003 Christy et al.
6,610,074 B2 8/2003 Santilli
6,620,193 B1 9/2003 Lau et al.
6,623,448 B2 9/2003 Slater
6,626,919 B1 9/2003 Swanstrom
6,632,229 B1 10/2003 Yamanouchi
6,638,286 B1 10/2003 Burbank et al.
6,652,521 B2 11/2003 Schulze
6,652,551 B1 11/2003 Heiss
6,656,194 B1 12/2003 Gannoe et al.
6,663,641 B1 12/2003 Kovac et al.
6,666,854 B1 12/2003 Lange
6,672,338 B1 1/2004 Esashi et al.
6,673,058 B2 1/2004 Snow
6,673,087 B1 1/2004 Chang et al.
6,679,882 B1 1/2004 Kornerup
6,685,628 B2 2/2004 Vu
6,685,724 B1 2/2004 Haluck
6,692,445 B2 2/2004 Roberts et al.
6,692,462 B2 2/2004 Mackenzie et al.
6,699,180 B2 3/2004 Kobayashi
6,699,256 B1 3/2004 Logan et al.
6,699,263 B2 3/2004 Cope
6,706,018 B2 3/2004 Westlund et al.
6,708,066 B2 3/2004 Herbst et al.
6,709,445 B2 3/2004 Boebel et al.
6,716,226 B2 4/2004 Sixto, Jr. et al.
6,736,822 B2 5/2004 McClellan et al.
6,740,030 B2 5/2004 Martone et al.
6,743,240 B2 6/2004 Smith et al.
6,749,560 B1 6/2004 Konstorum et al.
6,749,609 B1 6/2004 Lunsford et al.
6,752,768 B2 6/2004 Burdorff et al.
6,752,811 B2 6/2004 Chu et al.
6,752,822 B2 6/2004 Jespersen
6,761,685 B2 7/2004 Adams et al.
6,761,718 B2 7/2004 Madsen
6,761,722 B2 7/2004 Cole et al.
6,773,434 B2 8/2004 Ciarrocca
6,780,151 B2 8/2004 Grabover et al.
6,780,352 B2 8/2004 Jacobson
6,783,491 B2 8/2004 Saadat et al.
6,786,864 B2 9/2004 Matsuura et al.
6,790,173 B2 9/2004 Saadat et al.
6,795,728 B2 9/2004 Chornenky et al.
6,800,056 B2 10/2004 Tartaglia et al.
6,808,491 B2 10/2004 Kortenbach et al.
6,824,548 B2 11/2004 Smith et al.
6,836,688 B2 12/2004 Ingle et al.
6,837,847 B2 1/2005 Ewers et al.
6,843,794 B2 1/2005 Sixto, Jr. et al.
6,861,250 B1 3/2005 Cole et al.
6,866,627 B2 3/2005 Nozue
6,878,106 B1 4/2005 Herrmann
6,878,110 B2 4/2005 Yang et al.
6,881,216 B2 4/2005 Di Caprio et al.
6,884,213 B2 4/2005 Raz et al.
6,887,255 B2 5/2005 Shimm
6,889,089 B2 5/2005 Behl et al.
6,896,683 B1 5/2005 Gadberry et al.
6,896,692 B2 5/2005 Ginn et al.
6,908,427 B2 6/2005 Fleener et al.
6,908,476 B2 6/2005 Jud et al.
6,916,284 B2 7/2005 Moriyama
6,918,871 B2 7/2005 Schulze
6,926,725 B2 8/2005 Cooke et al.
6,932,810 B2 8/2005 Ryan
6,932,824 B1 8/2005 Roop et al.
6,932,827 B2 8/2005 Cole
6,932,834 B2 8/2005 Lizardi et al.
6,939,327 B2 9/2005 Hall et al.
6,942,613 B2 9/2005 Ewers et al.
6,945,472 B2 9/2005 Wuttke et al.
6,945,979 B2 9/2005 Kortenbach et al.
6,955,683 B2 10/2005 Bonutti
6,958,035 B2 10/2005 Friedman et al.
6,960,162 B2 11/2005 Saadat et al.
6,960,163 B2 11/2005 Ewers et al.
6,962,587 B2 11/2005 Johnson et al.
6,964,662 B2 11/2005 Kidooka
6,966,909 B2 11/2005 Marshall et al.
6,966,919 B2 11/2005 Sixto, Jr. et al.
6,967,462 B1 11/2005 Landis
6,971,988 B2 12/2005 Orban, III
6,972,017 B2 12/2005 Smith et al.
6,974,411 B2 12/2005 Belson
6,976,992 B2 12/2005 Sachatello et al.
6,984,203 B2 1/2006 Tartaglia et al.
6,984,205 B2 1/2006 Gazdzinski
6,986,774 B2 1/2006 Middleman et al.
6,988,987 B2 1/2006 Ishikawa et al.
6,989,028 B2 1/2006 Lashinski et al.
6,991,627 B2 1/2006 Madhani et al.
6,991,631 B2 1/2006 Woloszko et al.
6,994,708 B2 2/2006 Manzo
6,997,931 B2 2/2006 Sauer et al.
7,000,818 B2 2/2006 Shelton, IV et al.
7,001,341 B2 2/2006 Gellman et al.
7,008,375 B2 3/2006 Weisel
7,009,634 B2 3/2006 Iddan et al.
7,010,340 B2 3/2006 Scarantino et al.
7,020,531 B1 3/2006 Colliou et al.
7,025,580 B2 4/2006 Heagy et al.
7,029,435 B2 4/2006 Nakao
7,029,438 B2 4/2006 Morin et al.
7,029,450 B2 4/2006 Gellman
7,035,680 B2 4/2006 Partridge et al.
7,037,290 B2 5/2006 Gardeski et al.
7,041,052 B2 5/2006 Saadat et al.
7,052,489 B2 5/2006 Griego et al.
7,060,024 B2 6/2006 Long et al.
7,060,025 B2 6/2006 Long et al.
7,063,697 B2 6/2006 Slater
7,063,715 B2 6/2006 Onuki et al.
7,066,879 B2 6/2006 Fowler et al.
7,066,936 B2 6/2006 Ryan
7,070,602 B2 7/2006 Smith et al.
7,076,305 B2 7/2006 Imran et al.
7,083,618 B2 8/2006 Couture et al.
7,083,620 B2 8/2006 Jahns et al.
7,083,629 B2 8/2006 Weller et al.
7,083,635 B2 8/2006 Ginn
7,087,071 B2 8/2006 Nicholas et al.
7,090,673 B2 8/2006 Dycus et al.
7,090,685 B2 8/2006 Kortenbach et al.
7,093,518 B2 8/2006 Gmeilbauer
7,101,371 B2 9/2006 Dycus et al.
7,101,372 B2 9/2006 Dycus et al.
7,101,373 B2 9/2006 Dycus et al.
7,105,000 B2 9/2006 McBrayer
7,105,005 B2 9/2006 Blake
7,108,703 B2 9/2006 Danitz et al.
7,112,208 B2 9/2006 Morris et al.
7,115,092 B2 10/2006 Park et al.
7,117,703 B2 10/2006 Kato et al.
7,118,531 B2 10/2006 Krill
7,118,578 B2 10/2006 West, Jr. et al.
7,118,587 B2 10/2006 Dycus et al.
7,128,708 B2 10/2006 Saadat et al.

(56) References Cited

U.S. PATENT DOCUMENTS

RE39,415 E 11/2006 Bales et al.
7,131,978 B2 11/2006 Sancoff et al.
7,131,979 B2 11/2006 DiCarlo et al.
7,131,980 B1 11/2006 Field et al.
7,137,980 B2 11/2006 Buysse et al.
7,137,981 B2 11/2006 Long
7,146,984 B2 12/2006 Stack et al.
7,147,650 B2 12/2006 Lee
7,150,097 B2 12/2006 Sremcich et al.
7,150,655 B2 12/2006 Mastrototaro et al.
7,152,488 B2 12/2006 Hedrich et al.
7,153,321 B2 12/2006 Andrews
7,163,525 B2 1/2007 Franer
7,172,714 B2 2/2007 Jacobson
7,179,254 B2 2/2007 Pendekanti et al.
7,188,627 B2 3/2007 Nelson et al.
7,195,612 B2 3/2007 Van Sloten et al.
7,195,631 B2 3/2007 Dumbauld
7,204,820 B2 4/2007 Akahoshi
7,208,005 B2 4/2007 Frecker et al.
7,211,092 B2 5/2007 Hughett
7,220,227 B2 5/2007 Sasaki et al.
7,223,272 B2 5/2007 Francere et al.
7,232,414 B2 6/2007 Gonzalez
7,232,445 B2 6/2007 Kortenbach et al.
7,241,290 B2 7/2007 Doyle et al.
7,244,228 B2 7/2007 Lubowski
7,250,027 B2 7/2007 Barry
7,252,660 B2 8/2007 Kunz
7,255,675 B2 8/2007 Gertner et al.
7,270,663 B2 9/2007 Nakao
7,294,139 B1 11/2007 Gengler
7,301,250 B2 11/2007 Cassel
7,306,597 B2 12/2007 Manzo
7,308,828 B2 12/2007 Hashimoto
7,318,802 B2 1/2008 Suzuki et al.
7,320,695 B2 1/2008 Carroll
7,322,934 B2 1/2008 Miyake et al.
7,323,006 B2 1/2008 Andreas et al.
7,329,256 B2 2/2008 Johnson et al.
7,329,257 B2 2/2008 Kanehira et al.
7,329,383 B2 2/2008 Stinson
7,344,536 B1 3/2008 Lunsford et al.
7,352,387 B2 4/2008 Yamamoto
7,364,582 B2 4/2008 Lee
7,371,215 B2 5/2008 Colliou et al.
7,381,216 B2 6/2008 Buzzard et al.
7,393,322 B2 7/2008 Wenchell
7,402,162 B2 7/2008 Ouchi
7,404,791 B2 7/2008 Linares et al.
7,413,563 B2 8/2008 Corcoran et al.
7,416,554 B2 8/2008 Lam et al.
7,422,590 B2 9/2008 Kupferschmid et al.
7,435,257 B2 10/2008 Lashinski et al.
7,452,327 B2 11/2008 Durgin et al.
7,455,208 B2 11/2008 Wales et al.
7,468,066 B2 12/2008 Vargas et al.
7,488,295 B2 2/2009 Burbank et al.
7,497,867 B2 3/2009 Lasner et al.
7,507,200 B2 3/2009 Okada
7,524,281 B2 4/2009 Chu et al.
7,534,228 B2 5/2009 Williams
7,540,872 B2 6/2009 Schechter et al.
7,544,203 B2 6/2009 Chin et al.
7,548,040 B2 6/2009 Lee et al.
7,549,564 B2 6/2009 Boudreaux
7,553,278 B2 6/2009 Kucklick
7,553,298 B2 6/2009 Hunt et al.
7,559,887 B2 7/2009 Dannan
7,559,916 B2 7/2009 Smith et al.
7,560,006 B2 7/2009 Rakos et al.
7,561,916 B2 7/2009 Hunt et al.
7,566,334 B2 7/2009 Christian et al.
7,575,144 B2 8/2009 Ortiz et al.
7,575,548 B2 8/2009 Takemoto et al.
7,579,550 B2 8/2009 Dayton et al.
7,582,096 B2 9/2009 Gellman et al.
7,588,177 B2 9/2009 Racenet
7,588,557 B2 9/2009 Nakao
7,618,398 B2 11/2009 Holman et al.
7,632,250 B2 12/2009 Smith et al.
7,635,373 B2 12/2009 Ortiz
7,637,903 B2 12/2009 Lentz et al.
7,651,483 B2 1/2010 Byrum et al.
7,651,509 B2 1/2010 Bojarski et al.
7,654,431 B2 2/2010 Hueil et al.
7,662,089 B2 2/2010 Okada et al.
7,666,180 B2 2/2010 Holsten et al.
7,674,259 B2 3/2010 Shadduck
7,713,189 B2 5/2010 Hanke
7,713,270 B2 5/2010 Suzuki
7,736,374 B2 6/2010 Vaughan et al.
7,744,615 B2 6/2010 Couture
7,758,577 B2 7/2010 Nobis et al.
7,762,998 B2 7/2010 Birk et al.
7,771,416 B2 8/2010 Spivey et al.
7,780,683 B2 8/2010 Roue et al.
7,780,691 B2 8/2010 Stefanchik
7,794,409 B2 9/2010 Damarati
7,794,475 B2 9/2010 Hess et al.
7,828,186 B2 11/2010 Wales
7,837,615 B2 11/2010 Le et al.
7,846,171 B2 12/2010 Kullas et al.
7,850,660 B2 12/2010 Uth et al.
7,857,183 B2 12/2010 Shelton, IV
7,862,546 B2 1/2011 Conlon et al.
7,867,216 B2 1/2011 Wahr et al.
7,892,220 B2 2/2011 Faller et al.
7,896,887 B2 3/2011 Rimbaugh et al.
7,909,809 B2 3/2011 Scopton et al.
7,914,513 B2 3/2011 Voorhees, Jr.
7,918,869 B2 4/2011 Saadat et al.
7,931,624 B2 4/2011 Smith et al.
7,945,332 B2 5/2011 Schechter
7,947,000 B2 5/2011 Vargas et al.
7,955,298 B2 6/2011 Carroll et al.
7,963,975 B2 6/2011 Criscuolo
7,988,685 B2 8/2011 Ziaie et al.
8,029,504 B2 10/2011 Long
8,037,591 B2 10/2011 Spivey et al.
8,075,587 B2 12/2011 Ginn
2001/0049497 A1 12/2001 Kalloo et al.
2002/0022771 A1 2/2002 Diokno et al.
2002/0022857 A1 2/2002 Goldsteen et al.
2002/0023353 A1 2/2002 Ting-Kung
2002/0029055 A1 3/2002 Bonutti
2002/0042562 A1 4/2002 Meron et al.
2002/0049439 A1 4/2002 Mulier et al.
2002/0068945 A1 6/2002 Sixto, Jr. et al.
2002/0078967 A1 6/2002 Sixto, Jr. et al.
2002/0082516 A1 6/2002 Stefanchik
2002/0095164 A1 7/2002 Andreas et al.
2002/0107530 A1 8/2002 Sauer et al.
2002/0133115 A1 9/2002 Gordon et al.
2002/0138086 A1 9/2002 Sixto, Jr. et al.
2002/0147456 A1 10/2002 Diduch et al.
2002/0183591 A1 12/2002 Matsuura et al.
2003/0023255 A1 1/2003 Miles et al.
2003/0036679 A1 2/2003 Kortenbach et al.
2003/0069602 A1 4/2003 Jacobs et al.
2003/0083681 A1 5/2003 Moutafis et al.
2003/0114732 A1 6/2003 Webler et al.
2003/0120257 A1 6/2003 Houston et al.
2003/0124009 A1 7/2003 Ravi et al.
2003/0130564 A1 7/2003 Martone et al.
2003/0130656 A1 7/2003 Levin
2003/0158521 A1 8/2003 Ameri
2003/0167062 A1 9/2003 Gambale et al.
2003/0171651 A1 9/2003 Page et al.
2003/0176880 A1 9/2003 Long et al.
2003/0216611 A1 11/2003 Vu
2003/0216615 A1 11/2003 Ouchi
2003/0220545 A1 11/2003 Ouchi
2003/0225312 A1 12/2003 Suzuki et al.

(56) References Cited

U.S. PATENT DOCUMENTS

2003/0225332 A1 12/2003 Okada et al.
2003/0229269 A1 12/2003 Humphrey
2003/0229371 A1 12/2003 Whitworth
2003/0236549 A1 12/2003 Bonadio et al.
2004/0002683 A1 1/2004 Nicholson et al.
2004/0034369 A1 2/2004 Sauer et al.
2004/0098007 A1 5/2004 Heiss
2004/0101456 A1 5/2004 Kuroshima et al.
2004/0116948 A1 6/2004 Sixto, Jr. et al.
2004/0127940 A1 7/2004 Ginn et al.
2004/0133077 A1 7/2004 Obenchain et al.
2004/0133089 A1 7/2004 Kilcoyne et al.
2004/0136779 A1 7/2004 Bhaskar
2004/0138525 A1 7/2004 Saadat et al.
2004/0138529 A1 7/2004 Wiltshire et al.
2004/0138587 A1 7/2004 Lyons, IV
2004/0161451 A1 8/2004 Pierce et al.
2004/0186350 A1 9/2004 Brenneman et al.
2004/0193009 A1 9/2004 Jaffe et al.
2004/0193146 A1 9/2004 Lee et al.
2004/0193186 A1 9/2004 Kortenbach et al.
2004/0193188 A1 9/2004 Francese
2004/0193189 A1 9/2004 Kortenbach et al.
2004/0193200 A1 9/2004 Dworschak et al.
2004/0199052 A1 10/2004 Banik et al.
2004/0206859 A1 10/2004 Chong et al.
2004/0210245 A1 10/2004 Erickson et al.
2004/0215058 A1 10/2004 Zirps et al.
2004/0225183 A1 11/2004 Michlitsch et al.
2004/0225186 A1 11/2004 Horne, Jr. et al.
2004/0230095 A1 11/2004 Stefanchik et al.
2004/0230096 A1 11/2004 Stefanchik et al.
2004/0230097 A1 11/2004 Stefanchik et al.
2004/0230161 A1 11/2004 Zeiner
2004/0249246 A1 12/2004 Campos
2004/0249367 A1 12/2004 Saadat et al.
2004/0249394 A1 12/2004 Morris et al.
2004/0249443 A1 12/2004 Shanley et al.
2005/0004515 A1 1/2005 Hart et al.
2005/0033265 A1 2/2005 Engel et al.
2005/0033277 A1 2/2005 Clague et al.
2005/0033319 A1 2/2005 Gambale et al.
2005/0033333 A1 2/2005 Smith et al.
2005/0043690 A1 2/2005 Todd
2005/0049616 A1 3/2005 Rivera et al.
2005/0065397 A1 3/2005 Saadat et al.
2005/0065517 A1 3/2005 Chin
2005/0070754 A1 3/2005 Nobis et al.
2005/0070763 A1 3/2005 Nobis et al.
2005/0070764 A1 3/2005 Nobis et al.
2005/0080413 A1 4/2005 Canady
2005/0085693 A1 4/2005 Belson et al.
2005/0085832 A1 4/2005 Sancoff et al.
2005/0090837 A1 4/2005 Sixto, Jr. et al.
2005/0090838 A1 4/2005 Sixto, Jr. et al.
2005/0101837 A1 5/2005 Kalloo et al.
2005/0101838 A1 5/2005 Camillocci et al.
2005/0101984 A1* 5/2005 Chanduszko et al. ........ 606/185
2005/0107663 A1 5/2005 Saadat et al.
2005/0107664 A1 5/2005 Kalloo et al.
2005/0110881 A1 5/2005 Glukhovsky et al.
2005/0113847 A1 5/2005 Gadberry et al.
2005/0119613 A1 6/2005 Moenning et al.
2005/0124855 A1 6/2005 Jaffe et al.
2005/0125010 A1 6/2005 Smith et al.
2005/0131279 A1 6/2005 Boulais et al.
2005/0131457 A1 6/2005 Douglas et al.
2005/0137454 A1 6/2005 Saadat et al.
2005/0143647 A1 6/2005 Minai et al.
2005/0143690 A1 6/2005 High
2005/0143774 A1 6/2005 Polo
2005/0143803 A1 6/2005 Watson et al.
2005/0148880 A1* 7/2005 Tower ........................... 600/470
2005/0149087 A1 7/2005 Ahlberg et al.
2005/0149096 A1 7/2005 Hilal et al.
2005/0159648 A1 7/2005 Freed
2005/0165272 A1 7/2005 Okada et al.
2005/0165378 A1 7/2005 Heinrich et al.
2005/0165411 A1 7/2005 Orban, III
2005/0165429 A1 7/2005 Douglas et al.
2005/0182429 A1 8/2005 Yamanouchi
2005/0192478 A1 9/2005 Williams et al.
2005/0192598 A1 9/2005 Johnson et al.
2005/0192602 A1 9/2005 Manzo
2005/0192654 A1 9/2005 Chanduszko et al.
2005/0209624 A1 9/2005 Vijay
2005/0215858 A1 9/2005 Vail, III
2005/0216050 A1 9/2005 Sepetka et al.
2005/0228406 A1 10/2005 Bose
2005/0234297 A1 10/2005 Devierre et al.
2005/0250983 A1 11/2005 Tremaglio et al.
2005/0250990 A1 11/2005 Le et al.
2005/0250993 A1 11/2005 Jaeger
2005/0251166 A1* 11/2005 Vaughan et al. .............. 606/153
2005/0251176 A1 11/2005 Swanstrom et al.
2005/0261674 A1 11/2005 Nobis et al.
2005/0267492 A1 12/2005 Poncet et al.
2005/0272975 A1 12/2005 McWeeney et al.
2005/0272977 A1 12/2005 Saadat et al.
2005/0273084 A1 12/2005 Hinman et al.
2005/0277945 A1 12/2005 Saadat et al.
2005/0277951 A1 12/2005 Smith et al.
2005/0277952 A1 12/2005 Arp et al.
2005/0277954 A1 12/2005 Smith et al.
2005/0277955 A1 12/2005 Palmer et al.
2005/0277956 A1 12/2005 Francese et al.
2005/0277957 A1 12/2005 Kuhns et al.
2005/0283118 A1 12/2005 Uth et al.
2005/0283119 A1 12/2005 Uth et al.
2005/0288555 A1 12/2005 Binmoeller
2006/0004406 A1 1/2006 Wehrstein et al.
2006/0004409 A1 1/2006 Nobis et al.
2006/0004410 A1 1/2006 Nobis et al.
2006/0015009 A1 1/2006 Jaffe et al.
2006/0020167 A1 1/2006 Sitzmann
2006/0020247 A1 1/2006 Kagan et al.
2006/0025654 A1 2/2006 Suzuki et al.
2006/0025781 A1 2/2006 Young et al.
2006/0025812 A1 2/2006 Shelton, IV
2006/0025819 A1 2/2006 Nobis et al.
2006/0036267 A1 2/2006 Saadat et al.
2006/0041188 A1 2/2006 Dirusso et al.
2006/0058582 A1 3/2006 Maahs et al.
2006/0058776 A1 3/2006 Bilsbury
2006/0069396 A1 3/2006 Meade et al.
2006/0069424 A1 3/2006 Acosta et al.
2006/0069425 A1 3/2006 Hillis et al.
2006/0074413 A1 4/2006 Behzadian
2006/0079890 A1 4/2006 Guerra
2006/0089528 A1 4/2006 Tartaglia et al.
2006/0095031 A1 5/2006 Ormsby
2006/0095060 A1 5/2006 Mayenberger et al.
2006/0100687 A1 5/2006 Fahey et al.
2006/0106423 A1 5/2006 Weisel et al.
2006/0111209 A1 5/2006 Hinman et al.
2006/0111210 A1 5/2006 Hinman et al.
2006/0111704 A1 5/2006 Brenneman et al.
2006/0129166 A1 6/2006 Lavelle
2006/0135962 A1 6/2006 Kick et al.
2006/0135971 A1 6/2006 Swanstrom et al.
2006/0135984 A1 6/2006 Kramer et al.
2006/0142644 A1 6/2006 Mulac et al.
2006/0142652 A1 6/2006 Keenan
2006/0142790 A1 6/2006 Gertner
2006/0142798 A1 6/2006 Holman et al.
2006/0149131 A1 7/2006 Or
2006/0149132 A1 7/2006 Iddan
2006/0149135 A1 7/2006 Paz
2006/0161190 A1 7/2006 Gadberry et al.
2006/0167416 A1 7/2006 Mathis et al.
2006/0167482 A1 7/2006 Swain et al.
2006/0178560 A1 8/2006 Saadat et al.
2006/0183975 A1 8/2006 Saadat et al.
2006/0184161 A1 8/2006 Maahs et al.

(56) References Cited

U.S. PATENT DOCUMENTS

2006/0189844 A1 8/2006 Tien
2006/0189845 A1 8/2006 Maahs et al.
2006/0190027 A1 8/2006 Downey
2006/0195084 A1 8/2006 Slater
2006/0200005 A1 9/2006 Bjork et al.
2006/0200169 A1 9/2006 Sniffin
2006/0200170 A1 9/2006 Aranyi
2006/0200199 A1 9/2006 Bonutti et al.
2006/0217665 A1 9/2006 Prosek
2006/0217697 A1 9/2006 Lau et al.
2006/0217742 A1 9/2006 Messerly et al.
2006/0217743 A1 9/2006 Messerly et al.
2006/0229639 A1 10/2006 Whitfield
2006/0229640 A1 10/2006 Whitfield
2006/0237022 A1 10/2006 Chen et al.
2006/0237023 A1 10/2006 Cox et al.
2006/0241570 A1 10/2006 Wilk
2006/0247576 A1* 11/2006 Poncet .................... 604/164.01
2006/0247673 A1 11/2006 Voegele et al.
2006/0253004 A1 11/2006 Frisch et al.
2006/0253039 A1 11/2006 McKenna et al.
2006/0258907 A1 11/2006 Stefanchik et al.
2006/0258908 A1 11/2006 Stefanchik et al.
2006/0258910 A1 11/2006 Stefanchik et al.
2006/0258954 A1 11/2006 Timberlake et al.
2006/0258955 A1 11/2006 Hoffman et al.
2006/0259010 A1 11/2006 Stefanchik et al.
2006/0264752 A1 11/2006 Rubinsky et al.
2006/0264904 A1 11/2006 Kerby et al.
2006/0264930 A1 11/2006 Nishimura
2006/0270902 A1 11/2006 Igarashi et al.
2006/0271102 A1 11/2006 Bosshard et al.
2006/0276835 A1 12/2006 Uchida
2006/0281970 A1 12/2006 Stokes et al.
2006/0282106 A1 12/2006 Cole et al.
2006/0285732 A1 12/2006 Horn et al.
2006/0287644 A1 12/2006 Inganas et al.
2006/0287666 A1 12/2006 Saadat et al.
2006/0293626 A1 12/2006 Byrum et al.
2007/0002135 A1 1/2007 Glukhovsky
2007/0005019 A1 1/2007 Okishige
2007/0010801 A1 1/2007 Chen et al.
2007/0015965 A1 1/2007 Cox et al.
2007/0016255 A1 1/2007 Korb et al.
2007/0032700 A1 2/2007 Fowler et al.
2007/0032701 A1 2/2007 Fowler et al.
2007/0043261 A1 2/2007 Watanabe et al.
2007/0043345 A1 2/2007 Davalos et al.
2007/0049800 A1 3/2007 Boulais
2007/0049902 A1 3/2007 Griffin et al.
2007/0051375 A1 3/2007 Milliman
2007/0060880 A1 3/2007 Gregorich et al.
2007/0067017 A1 3/2007 Trapp
2007/0073102 A1 3/2007 Matsuno et al.
2007/0073269 A1 3/2007 Becker
2007/0079924 A1 4/2007 Saadat et al.
2007/0088370 A1 4/2007 Kahle et al.
2007/0100375 A1 5/2007 Mikkaichi et al.
2007/0100376 A1 5/2007 Mikkaichi et al.
2007/0106118 A1 5/2007 Moriyama
2007/0112251 A1 5/2007 Nakhuda
2007/0112331 A1 5/2007 Weber et al.
2007/0112342 A1 5/2007 Pearson et al.
2007/0112383 A1 5/2007 Conlon et al.
2007/0112384 A1 5/2007 Conlon et al.
2007/0112385 A1 5/2007 Conlon
2007/0112417 A1 5/2007 Shanley et al.
2007/0112425 A1 5/2007 Schaller et al.
2007/0118115 A1 5/2007 Artale et al.
2007/0123840 A1 5/2007 Cox
2007/0129605 A1 6/2007 Schaaf
2007/0129719 A1 6/2007 Kendale et al.
2007/0129760 A1 6/2007 Demarais et al.
2007/0135709 A1 6/2007 Rioux et al.
2007/0135803 A1 6/2007 Belson
2007/0142706 A1 6/2007 Matsui et al.
2007/0142780 A1 6/2007 Van Lue
2007/0154460 A1 7/2007 Kraft et al.
2007/0156028 A1 7/2007 Van Lue et al.
2007/0156127 A1 7/2007 Rioux et al.
2007/0161855 A1 7/2007 Mikkaichi et al.
2007/0162101 A1 7/2007 Burgermeister et al.
2007/0173691 A1 7/2007 Yokoi et al.
2007/0173869 A1 7/2007 Gannoe et al.
2007/0173870 A2 7/2007 Zacharias
2007/0173872 A1 7/2007 Neuenfeldt
2007/0179525 A1 8/2007 Frecker et al.
2007/0179530 A1 8/2007 Tieu et al.
2007/0197865 A1 8/2007 Miyake et al.
2007/0198057 A1 8/2007 Gelbart et al.
2007/0203487 A1 8/2007 Sugita
2007/0208336 A1 9/2007 Kim et al.
2007/0208364 A1 9/2007 Smith et al.
2007/0213754 A1 9/2007 Mikkaichi et al.
2007/0225554 A1 9/2007 Maseda et al.
2007/0233040 A1 10/2007 Macnamara et al.
2007/0244358 A1 10/2007 Lee
2007/0250038 A1 10/2007 Boulais
2007/0250057 A1 10/2007 Nobis et al.
2007/0255096 A1 11/2007 Stefanchik et al.
2007/0255100 A1 11/2007 Barlow et al.
2007/0255273 A1 11/2007 Fernandez et al.
2007/0255303 A1 11/2007 Bakos et al.
2007/0255306 A1* 11/2007 Conlon et al. ................ 606/192
2007/0260112 A1 11/2007 Rahmani
2007/0260117 A1 11/2007 Zwolinski et al.
2007/0260121 A1 11/2007 Bakos et al.
2007/0260273 A1 11/2007 Cropper et al.
2007/0270629 A1 11/2007 Charles
2007/0270889 A1 11/2007 Conlon et al.
2007/0270895 A1 11/2007 Nobis et al.
2007/0270907 A1 11/2007 Stokes et al.
2007/0282371 A1 12/2007 Lee et al.
2007/0293727 A1 12/2007 Goldfarb et al.
2007/0299387 A1 12/2007 Williams et al.
2008/0004650 A1 1/2008 George
2008/0015409 A1 1/2008 Barlow et al.
2008/0015552 A1 1/2008 Doyle et al.
2008/0021416 A1 1/2008 Arai et al.
2008/0022927 A1 1/2008 Zhang et al.
2008/0027387 A1 1/2008 Grabinsky
2008/0033451 A1 2/2008 Rieber et al.
2008/0051629 A1 2/2008 Sugiyama et al.
2008/0051735 A1 2/2008 Measamer et al.
2008/0058586 A1 3/2008 Karpiel
2008/0065169 A1 3/2008 Colliou et al.
2008/0071264 A1 3/2008 Azure
2008/0086172 A1 4/2008 Martin et al.
2008/0097159 A1 4/2008 Ishiguro
2008/0097472 A1 4/2008 Agmon et al.
2008/0097483 A1 4/2008 Ortiz et al.
2008/0103527 A1 5/2008 Martin et al.
2008/0114384 A1 5/2008 Chang et al.
2008/0119870 A1 5/2008 Williams
2008/0119891 A1 5/2008 Miles et al.
2008/0125796 A1 5/2008 Graham
2008/0132892 A1 6/2008 Lunsford et al.
2008/0139882 A1 6/2008 Fujimori
2008/0147113 A1 6/2008 Nobis et al.
2008/0171907 A1 7/2008 Long et al.
2008/0177135 A1 7/2008 Muyari et al.
2008/0188868 A1 8/2008 Weitzner et al.
2008/0200755 A1 8/2008 Bakos
2008/0200762 A1 8/2008 Stokes et al.
2008/0200911 A1 8/2008 Long
2008/0200912 A1 8/2008 Long
2008/0200933 A1 8/2008 Bakos et al.
2008/0200934 A1 8/2008 Fox
2008/0208213 A1 8/2008 Benjamin et al.
2008/0221587 A1 9/2008 Schwartz
2008/0221619 A1 9/2008 Spivey et al.
2008/0228213 A1 9/2008 Blakeney et al.
2008/0230972 A1 9/2008 Ganley
2008/0234696 A1 9/2008 Taylor et al.

(56) References Cited

U.S. PATENT DOCUMENTS

2008/0243106 A1 10/2008 Coe et al.
2008/0243148 A1 10/2008 Mikkaichi et al.
2008/0243176 A1 10/2008 Weitzner et al.
2008/0249567 A1 10/2008 Kaplan
2008/0262540 A1 10/2008 Bangera et al.
2008/0269782 A1 10/2008 Stefanchik et al.
2008/0269783 A1 10/2008 Griffith
2008/0275474 A1 11/2008 Martin et al.
2008/0275475 A1 11/2008 Schwemberger et al.
2008/0287737 A1 11/2008 Dejima
2008/0287983 A1 11/2008 Smith et al.
2008/0300461 A1 12/2008 Shaw et al.
2008/0300547 A1 12/2008 Bakos
2008/0309758 A1 12/2008 Karasawa et al.
2008/0312496 A1 12/2008 Zwolinski
2008/0312499 A1 12/2008 Handa et al.
2008/0312500 A1 12/2008 Asada et al.
2008/0312506 A1 12/2008 Spivey et al.
2008/0319436 A1 12/2008 Daniel et al.
2008/0319439 A1 12/2008 Ootsubu
2009/0054728 A1 2/2009 Trusty
2009/0062788 A1 3/2009 Long et al.
2009/0062792 A1 3/2009 Vakharia et al.
2009/0062795 A1 3/2009 Vakharia et al.
2009/0069634 A1 3/2009 Larkin
2009/0076499 A1 3/2009 Azure
2009/0078736 A1 3/2009 Van Lue
2009/0082776 A1 3/2009 Cresina
2009/0082779 A1 3/2009 Nakao
2009/0105654 A1* 4/2009 Kurth et al. ............. 604/170.03
2009/0112059 A1 4/2009 Nobis
2009/0112062 A1 4/2009 Bakos
2009/0112063 A1 4/2009 Bakos et al.
2009/0125042 A1 5/2009 Mouw
2009/0131751 A1 5/2009 Spivey et al.
2009/0131932 A1 5/2009 Vakharia et al.
2009/0131933 A1 5/2009 Ghabrial et al.
2009/0143639 A1 6/2009 Stark
2009/0143649 A1 6/2009 Rossi
2009/0143794 A1 6/2009 Conlon et al.
2009/0143818 A1 6/2009 Faller et al.
2009/0149710 A1 6/2009 Stefanchik et al.
2009/0177031 A1 7/2009 Surti et al.
2009/0177219 A1 7/2009 Conlon
2009/0182332 A1 7/2009 Long et al.
2009/0192344 A1 7/2009 Bakos et al.
2009/0192534 A1 7/2009 Ortiz et al.
2009/0198231 A1 8/2009 Esser et al.
2009/0198253 A1 8/2009 Omori
2009/0216248 A1 8/2009 Uenohara et al.
2009/0227828 A1 9/2009 Swain et al.
2009/0248055 A1 10/2009 Spivey et al.
2009/0281559 A1 11/2009 Swain et al.
2009/0287206 A1 11/2009 Jun
2009/0287236 A1 11/2009 Bakos et al.
2009/0292164 A1 11/2009 Yamatani
2009/0299135 A1 12/2009 Spivey
2009/0299143 A1 12/2009 Conlon et al.
2009/0299362 A1 12/2009 Long et al.
2009/0299385 A1 12/2009 Stefanchik et al.
2009/0299406 A1 12/2009 Swain et al.
2009/0299409 A1 12/2009 Coe et al.
2009/0306658 A1 12/2009 Nobis et al.
2009/0306683 A1 12/2009 Zwolinski et al.
2009/0322864 A1 12/2009 Karasawa et al.
2009/0326561 A1 12/2009 Carroll, II et al.
2010/0010294 A1 1/2010 Conlon et al.
2010/0010298 A1 1/2010 Bakos et al.
2010/0010299 A1 1/2010 Bakos et al.
2010/0010303 A1 1/2010 Bakos
2010/0010510 A1 1/2010 Stefanchik
2010/0010511 A1 1/2010 Harris et al.
2010/0023032 A1 1/2010 Granja Filho
2010/0036198 A1 2/2010 Tacchino et al.
2010/0042045 A1 2/2010 Splvey
2010/0048990 A1 2/2010 Bakos
2010/0049190 A1 2/2010 Long et al.
2010/0049223 A1 2/2010 Granja Filho
2010/0056861 A1 3/2010 Spivey
2010/0056862 A1 3/2010 Bakos
2010/0057085 A1 3/2010 Holcomb et al.
2010/0057108 A1 3/2010 Spivey et al.
2010/0063538 A1 3/2010 Spivey et al.
2010/0076451 A1 3/2010 Zwolinski et al.
2010/0081877 A1 4/2010 Vakharia
2010/0113872 A1 5/2010 Asada et al.
2010/0121362 A1 5/2010 Clague et al.
2010/0130817 A1 5/2010 Conlon
2010/0130975 A1 5/2010 Long
2010/0131005 A1 5/2010 Conlon
2010/0152539 A1 6/2010 Ghabrial et al.
2010/0152609 A1 6/2010 Zwolinski et al.
2010/0152746 A1 6/2010 Ceniccola et al.
2010/0179510 A1 7/2010 Fox et al.
2010/0179530 A1 7/2010 Long et al.
2010/0191050 A1 7/2010 Zwolinski
2010/0191267 A1 7/2010 Fox
2010/0198005 A1 8/2010 Fox
2010/0198248 A1 8/2010 Vakharia
2010/0249700 A1 9/2010 Spivey
2010/0286791 A1 11/2010 Goldsmith
2010/0298642 A1 11/2010 Trusty et al.
2010/0312056 A1 12/2010 Galperin et al.
2010/0331622 A2 12/2010 Conlon
2010/0331774 A2 12/2010 Spivey
2011/0093009 A1 4/2011 Fox
2011/0098694 A1 4/2011 Long
2011/0098704 A1 4/2011 Long et al.
2011/0105850 A1 5/2011 Voegele et al.
2011/0112434 A1 5/2011 Ghabrial et al.
2011/0115891 A1 5/2011 Trusty
2011/0124964 A1 5/2011 Nobis
2011/0152609 A1 6/2011 Trusty et al.
2011/0152610 A1 6/2011 Trusty et al.
2011/0152612 A1 6/2011 Trusty et al.
2011/0152858 A1 6/2011 Long et al.
2011/0152859 A1 6/2011 Long et al.
2011/0152878 A1 6/2011 Trusty et al.
2011/0152923 A1 6/2011 Fox
2011/0160514 A1 6/2011 Long et al.
2011/0190659 A1 8/2011 Long et al.
2011/0190764 A1 8/2011 Long et al.
2011/0245619 A1 10/2011 Holcomb
2011/0306971 A1 12/2011 Long
2012/0004502 A1 1/2012 Weitzner et al.

FOREIGN PATENT DOCUMENTS

DE 4323585 A1 1/1995
DE 19713797 A1 10/1997
DE 19757056 B4 8/2008
DE 102006027873 B4 10/2009
EP 0086338 A1 8/1983
EP 0286415 A2 10/1988
EP 0589454 A2 3/1994
EP 0464479 B1 3/1995
EP 0529675 B1 2/1996
EP 0724863 B1 7/1999
EP 0760629 B1 11/1999
EP 0818974 B1 7/2001
EP 1281356 A2 2/2003
EP 0947166 B1 5/2003
EP 0836832 B1 12/2003
EP 1402837 A1 3/2004
EP 0744918 B1 4/2004
EP 0931515 B1 8/2004
EP 0941128 B1 10/2004
EP 1411843 B1 10/2004
EP 1150614 B1 11/2004
EP 1477104 A1 11/2004
EP 1481642 A1 12/2004
EP 1493391 A1 1/2005
EP 0848598 B1 2/2005
EP 1281360 B1 3/2005

(56) References Cited

FOREIGN PATENT DOCUMENTS

| | | | |
|---|---|---|---|
| EP | 1568330 | A1 | 8/2005 |
| EP | 1452143 | B1 | 9/2005 |
| EP | 1616527 | A2 | 1/2006 |
| EP | 1006888 | B1 | 3/2006 |
| EP | 1629764 | A1 | 3/2006 |
| EP | 1013229 | B1 | 6/2006 |
| EP | 1721561 | A1 | 11/2006 |
| EP | 1153578 | B1 | 3/2007 |
| EP | 1334696 | B1 | 3/2007 |
| EP | 1769766 | A1 | 4/2007 |
| EP | 1836971 | A2 | 9/2007 |
| EP | 1836980 | A1 | 9/2007 |
| EP | 1854421 | A2 | 11/2007 |
| EP | 1857061 | A1 | 11/2007 |
| EP | 1875876 | A1 | 1/2008 |
| EP | 1891881 | A1 | 2/2008 |
| EP | 1902663 | A1 | 3/2008 |
| EP | 1477106 | B1 | 6/2008 |
| EP | 1949844 | A1 | 7/2008 |
| EP | 1518499 | B1 | 8/2008 |
| EP | 1709918 | B1 | 10/2008 |
| EP | 1985226 | A2 | 10/2008 |
| EP | 1994904 | A1 | 11/2008 |
| EP | 1707130 | B1 | 12/2008 |
| EP | 0723462 | B1 | 3/2009 |
| EP | 1769749 | B1 | 11/2009 |
| EP | 1493397 | B1 | 9/2011 |
| FR | 2731610 | A1 | 9/1996 |
| GB | 330629 | A | 6/1930 |
| GB | 2335860 | A | 10/1999 |
| GB | 2403909 | A | 1/2005 |
| GB | 2421190 | A | 6/2006 |
| GB | 2443261 | A | 4/2008 |
| JP | 56-46674 | | 4/1981 |
| JP | 63309252 | A | 12/1988 |
| JP | 4038960 | A | 2/1992 |
| JP | 8-29699 | A | 2/1996 |
| JP | 2000245683 | A | 9/2000 |
| JP | 2002-369791 | A | 12/2002 |
| JP | 2003-088494 | A | 3/2003 |
| JP | 2003-235852 | A | 8/2003 |
| JP | 2004-33525 | A | 2/2004 |
| JP | 2004-065745 | A | 3/2004 |
| JP | 2005-121947 | A | 5/2005 |
| JP | 2005-261514 | A | 9/2005 |
| JP | 2006297005 | A | 11/2006 |
| NL | 1021295 | C2 | 2/2004 |
| SU | 194230 | | 5/1967 |
| SU | 980703 | | 12/1982 |
| WO | WO 84/01707 | A1 | 5/1984 |
| WO | WO 92/13494 | A1 | 8/1992 |
| WO | WO 93/10850 | A1 | 6/1993 |
| WO | WO 93/20760 | A1 | 10/1993 |
| WO | WO 93/20765 | A1 | 10/1993 |
| WO | WO 95/09666 | A1 | 4/1995 |
| WO | WO 96/22056 | A1 | 7/1996 |
| WO | WO 96/27331 | A1 | 9/1996 |
| WO | WO 96/39946 | A1 | 12/1996 |
| WO | WO 97/12557 | A1 | 4/1997 |
| WO | WO 98/01080 | A1 | 1/1998 |
| WO | WO 99/00060 | A1 | 1/1999 |
| WO | WO 99/09919 | A1 | 3/1999 |
| WO | WO 99/17661 | A1 | 4/1999 |
| WO | WO 99/30622 | A2 | 6/1999 |
| WO | WO 00/35358 | A1 | 6/2000 |
| WO | WO 01/10319 | A1 | 2/2001 |
| WO | WO 01/26708 | A1 | 4/2001 |
| WO | WO 01/41627 | A2 | 6/2001 |
| WO | WO 01/58360 | A2 | 8/2001 |
| WO | WO 02/11621 | A1 | 2/2002 |
| WO | WO 02/34122 | A2 | 5/2002 |
| WO | WO 02/094082 | A2 | 11/2002 |
| WO | WO 03/045260 | A1 | 6/2003 |
| WO | WO 03/047684 | A2 | 6/2003 |
| WO | WO 03/059412 | A2 | 7/2003 |
| WO | WO 03/078721 | A2 | 9/2003 |
| WO | WO 03/081761 | A2 | 10/2003 |
| WO | WO 03/082129 | A2 | 10/2003 |
| WO | WO 2004/006789 | A1 | 1/2004 |
| WO | WO 2004/028613 | A2 | 4/2004 |
| WO | WO 2004/037123 | A1 | 5/2004 |
| WO | WO 2004/037149 | A1 | 5/2004 |
| WO | WO 2004/052221 | A1 | 6/2004 |
| WO | WO 2004/086984 | A1 | 10/2004 |
| WO | WO 2005/009211 | A2 | 2/2005 |
| WO | WO 2005/018467 | A2 | 3/2005 |
| WO | WO 2005/037088 | A2 | 4/2005 |
| WO | WO 2005/048827 | A1 | 6/2005 |
| WO | WO 2005/065284 | A2 | 7/2005 |
| WO | WO 2005/097019 | A2 | 10/2005 |
| WO | WO 2005/097234 | A2 | 10/2005 |
| WO | WO 2005/112810 | A2 | 12/2005 |
| WO | WO 2005/120363 | A1 | 12/2005 |
| WO | WO 2006/007399 | A1 | 1/2006 |
| WO | WO 2006/012630 | A2 | 2/2006 |
| WO | WO 2006/040109 | A1 | 4/2006 |
| WO | WO 2006/041881 | A2 | 4/2006 |
| WO | WO 2006/060405 | A2 | 6/2006 |
| WO | WO 2006/110733 | A2 | 10/2006 |
| WO | WO 2006/113216 | A2 | 10/2006 |
| WO | WO 2007/013059 | A2 | 2/2007 |
| WO | WO 2007/014063 | A2 | 2/2007 |
| WO | WO 2007/048085 | A2 | 4/2007 |
| WO | WO 2007/063550 | A2 | 6/2007 |
| WO | WO 2007/100067 | A1 | 9/2007 |
| WO | WO 2007/109171 | A2 | 9/2007 |
| WO | WO 2008/005433 | A1 | 1/2008 |
| WO | WO 2008/033356 | A2 | 3/2008 |
| WO | WO 2008/041225 | A2 | 4/2008 |
| WO | WO 2008/076337 | A1 | 6/2008 |
| WO | WO 2008/076800 | A2 | 6/2008 |
| WO | WO 2008/079440 | A2 | 7/2008 |
| WO | WO 2008/101075 | A2 | 8/2008 |
| WO | WO 2008/102154 | A2 | 8/2008 |
| WO | WO 2008/108863 | A2 | 9/2008 |
| WO | WO 2008/151237 | A1 | 12/2008 |
| WO | WO 2009/021030 | A1 | 2/2009 |
| WO | WO 2009/027065 | A1 | 3/2009 |
| WO | WO 2009/029065 | A1 | 3/2009 |
| WO | WO 2009/032623 | A2 | 3/2009 |
| WO | WO 2009/121017 | A1 | 10/2009 |
| WO | WO 2010/027688 | A1 | 3/2010 |
| WO | WO 2010/080974 | A1 | 7/2010 |
| WO | WO 2010/088481 | A1 | 8/2010 |

OTHER PUBLICATIONS

Ethicon, Inc., "Wound Closure Manual: Chapter 3 (The Surgical Needle)," 15 pages, (publication date unknown).

Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.

Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.

Ogando, "Prototype Tools That Go With the Flow," Design News, 2 pages, Jul. 17, 2006.

Edd, et al., "In Vivo Results of a New Focal Tissue Ablation Technique: Irreversible Electroporation," IEEE Trans Biomed Eng, vol. 53, pp. 1409-1415, 2006.

Kennedy, et al., "High-Burst-Strength, Feedback-Controlled Bipolar Vessel Sealing," Surgical Endoscopy, vol. 12, pp. 876-878 (1998).

Collins et al., "Local Gene Therapy of Solid Tumors with GM-CSF and B7-1 Eradicates Both Treated and Distal Tumors," Cancer Gene Therapy, vol. 13, pp. 1061-1071 (2006).

K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).

K. Sumiyama et al., "Submucosal Endoscopy with Mucosal Flap Safety Valve," Gastrointest Endosc. Apr. 2007, vol. 65(4) pp. 694-695 (Abstract).

(56) References Cited

OTHER PUBLICATIONS

K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du Feb. 24, 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. 2007, pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRelId=1000.1003&method=D . . . , accessed Jul. 18, 2008 (4 pages).
U.S. Appl. No. 11/894,358, filed Aug. 21, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489, filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 12/060,601, filed Apr. 1, 2008.
U.S. Appl. No. 11/952,475, filed Dec. 7, 2007.
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
International Search Report and Written Opinion for PCT/US2010/022177, May 11, 2010 (14 pages).
International Preliminary Report on Patentability for PCT/US2010/022177, Aug. 2, 2011 (7 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.

(56) References Cited

OTHER PUBLICATIONS

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation in Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/a11/20090422_152000; accessed Aug. 28, 2009 (3 pages).
"Ethicon Endo-Surgery Studies Presented At DDW Demonstrate Potential of Pure Notes Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal Notes Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
Zadno et al., "Linear Superelasticity in Cold-Worked NI-TI," Engineering Aspects of Shape Memory Alloys, pp. 414-419 (1990).
U.S. Appl. No. 13/218,221, filed Aug. 25, 2011.
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
U.S. Appl. No. 13/036,895, filed Feb. 28, 2011.
U.S. Appl. No. 13/036,908, filed Feb. 28, 2011.
U.S. Appl. No. 13/267,251, filed Oct. 6, 2011.
U.S. Appl. No. 13/325,791, filed Dec. 14, 2011.
U.S. Appl. No. 13/352,495, filed Jan. 18, 2012.
U.S. Appl. No. 13/399,358, filed Feb. 17, 2012.
U.S. Appl. No. 13/420,805, filed Mar. 15, 2012.
U.S. Appl. No. 13/420,818, filed Mar. 15, 2012.
U.S. Appl. No. 13/425,103, filed Mar. 20, 2012.

* cited by examiner

Fluid Source
14
15
9
17
11
16
12
13
22
7
5
11
13
21
12
20
18

12
18
16
11
28
26
24
17
5
28
13
CW
15
34
30
32
14

SURGICAL DEVICE

BACKGROUND

Endoscopy refers to looking inside a human body for medical reasons using an instrument called an endoscope. Endoscopy is a minimally invasive diagnostic medical procedure used to evaluate interior surfaces of an organ or other tissue by inserting a small tube into the body, often, but not necessarily, through a natural body opening of a patient or through a relatively small incision. Using the endoscope, a surgeon may view surface conditions of the organs or other tissue, including abnormal or diseased tissue such as lesions and other various surface conditions. The endoscope may have a rigid or a flexible tube and, in addition to providing an image for visual inspection and photography, the endoscope may be adapted and configured for taking biopsies, retrieving foreign objects, and introducing medical instruments to a tissue treatment region, referred to generally herein as a surgical site.

Laparoscopic surgery is a minimally invasive surgical technique in which operations are performed through small incisions (usually 0.5 cm to 1.5 cm) or keyholes, as compared to the larger incisions required in traditional open-type surgical procedures. Laparoscopic surgery includes operations within the abdominal or pelvic cavities, whereas keyhole surgery performed on the thoracic or chest cavity is called thoracoscopic surgery. Laparoscopic and thoracoscopic surgery belong to the broader field of endoscopy.

A key element in laparoscopic surgery is the use of a laparoscope: a telescopic rod lens system that is usually connected to a video camera (single-chip or three-chip). Also attached is a fiber-optic cable system connected to a "cold" light source (halogen or xenon) to illuminate the operative field and configured to be inserted through a 5 mm or 10 mm cannula to view the surgical site. The abdomen is usually insufflated with carbon dioxide gas to create a working and viewing space for a surgeon. Stated another way, the abdomen is essentially blown up like a balloon (i.e., insufflated) thereby elevating the abdominal wall above the internal organs like a dome. Carbon dioxide gas can be used for the insufflation because it is common to the patient's body and can be removed by the respiratory system if it is absorbed through tissue.

Minimally invasive therapeutic procedures used to treat diseased tissue by introducing medical instruments to the surgical site through a natural opening of a patient are known as Natural Orifice Translumenal Endoscopic Surgery (NOTES™). In general, there are a variety of systems for inserting an endoscope through a natural opening in the human body, dissecting a lumen, and then, treating the inside of the abdominal cavity. For example, in U.S. Pat. No. 5,297,536 to Wilk, issued on Mar. 29, 1994, which is hereby incorporated by reference in its entirety, a sample treatment system is disclosed. This system is comprised of a dissecting device for perforating a lumen wall, an endoscope insert member for inserting an endoscope, a tube, an endoscope, and a pneumoperitoneum device for deflating the abdominal cavity, and a closing device.

When transluminal endoscopic surgery is carried out using the above-referenced system, an overtube can first be inserted through a natural opening in the patient's body (e.g., mouth, anus, or vagina). A distal end of the overtube may be attached to an organ wall or other tissue by vacuum pressure, thus being temporarily fixed thereon such that the organ wall or other tissue can be punctured. An incising instrument, such as a needle, for example, may be passed through the overtube from a proximal end of the overtube to a distal end of the overtube, and/or through a working channel of the endoscope, and used to puncture and create an opening through the organ wall or other tissue. An inflatable member, such as a medical balloon, for example, may be positioned in the opening and then inflated to enlarge the opening. Once the opening has been enlarged by the inflatable member, the inflatable member can be at least partially deflated and removed from the body and the overtube may then be inserted into and partially through the opening to serve as a working channel for the endoscope and/or other surgical instruments or devices to the surgical site. After surgery of the inside of the organ or other tissue is complete, the overtube may be removed from the enlarged opening so that the opening can be closed by an O-ring or other suitable closure device and then the endoscope and the overtube may be withdrawn from the body.

The peritoneum may be accessed through the stomach wall or wall of other hollow body organs or internal body lumens, to achieve surgical therapy or diagnostic procedures therein. To minimize the potential for inadvertent damage to underlying organs or tissues, the piercing process required in the translumenal access of the peritoneum needs to be safe and controllable at the distal tip of an endoscope. Accordingly, in the field of endoscopy, there remains a need for improved methods and devices for translumenal access of internal body cavities using a needle and an inflatable member, to pierce the internal body lumens during an endoscopic surgical procedure.

FIGURES

The novel features of the various embodiments are set forth with particularity in the appended claims. The various embodiments, however, both as to organization and methods of operation may best be understood by reference to the following description, taken in conjunction with the accompanying figures as follows.

Figure 1:
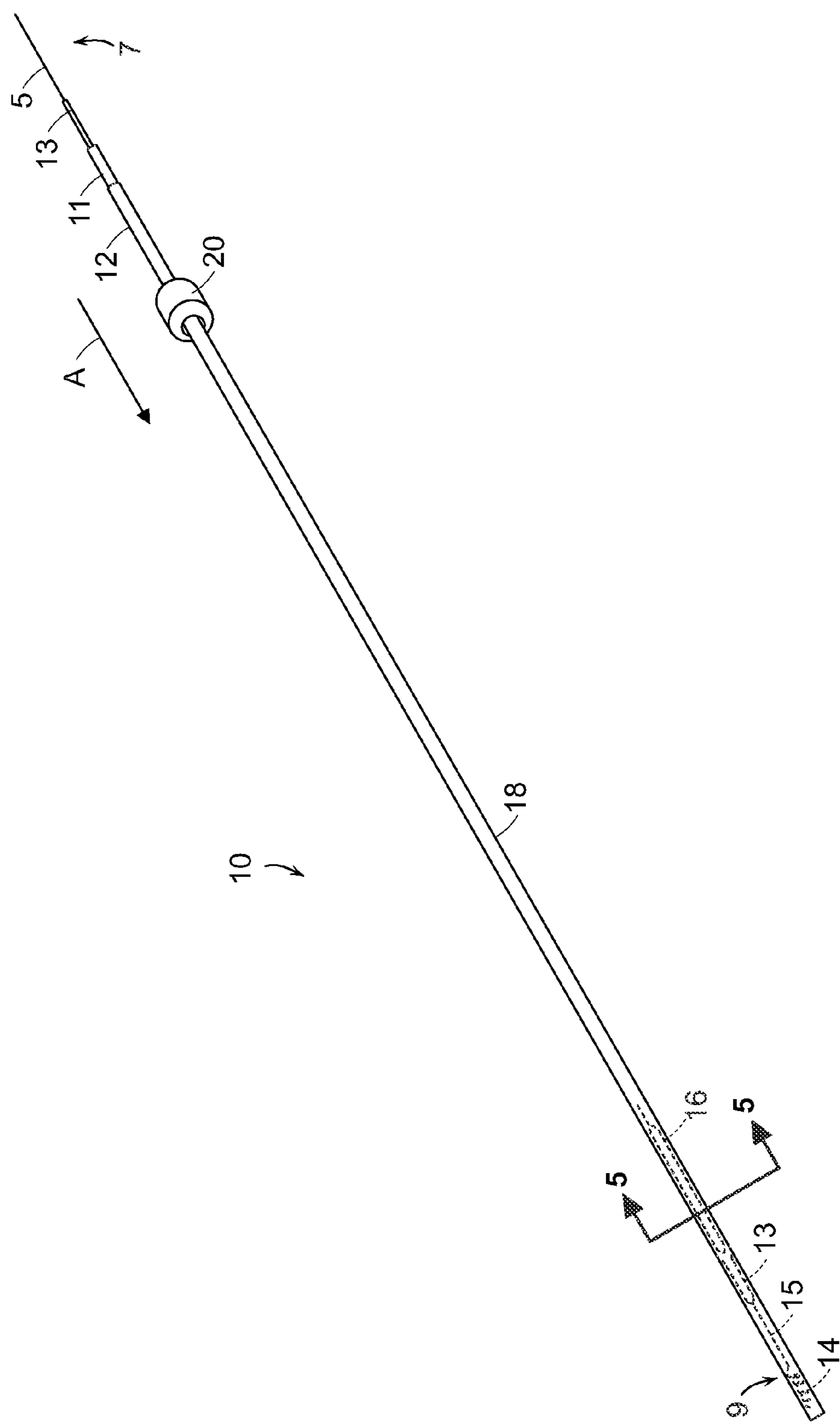
FIG. 1 illustrates a perspective view of one embodiment of a surgical device comprising a needle, an elongated guide wire, a conduit, an inflation conduit, an inflatable member, and a protective sleeve, which is shown in an extended or a first position.
Figure 15:
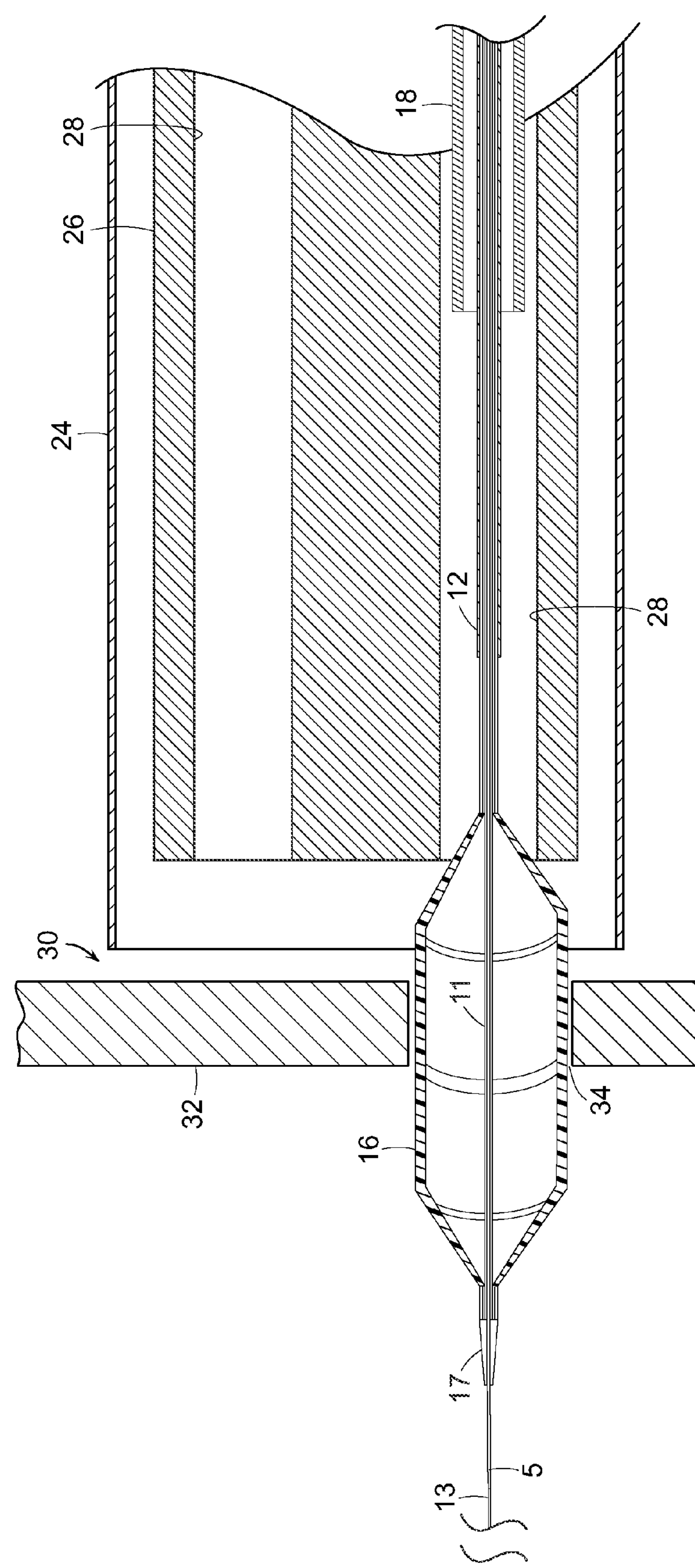
Figure 16:
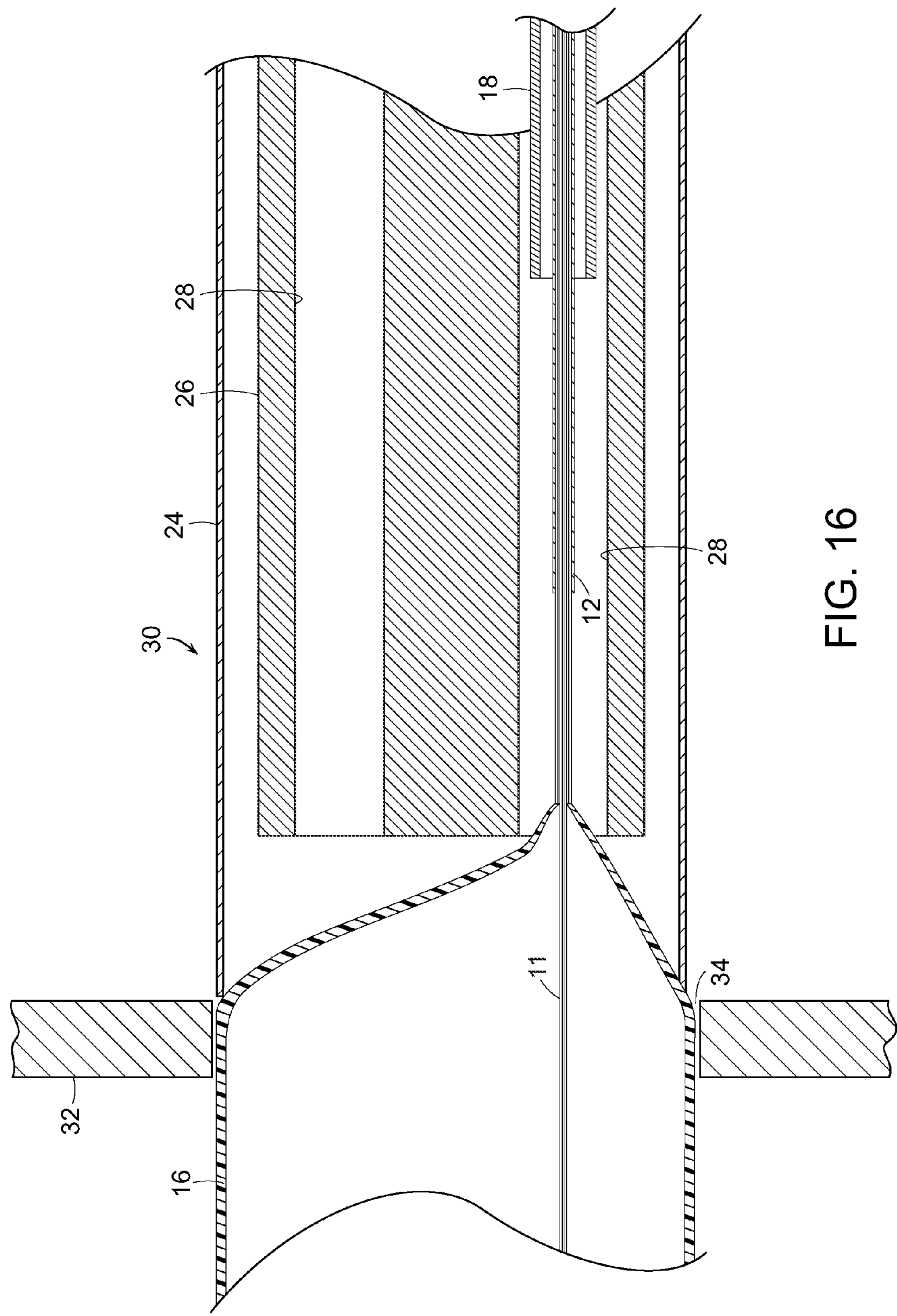

FIG. 15 illustrates a cross-sectional view of the distal portion of the surgical device of FIG. 1 after the protective sleeve has been retracted into the second position and with the inflatable member sufficiently inflated to expand the opening in accordance with one non-limiting embodiment FIG. 16 illustrates a cross-sectional view of the distal portion of one embodiment of the surgical device of FIG. 1 after the protective sleeve has been retracted into the second position and with the inflatable member inflated to expand the opening in the tissue.

Figure 17:
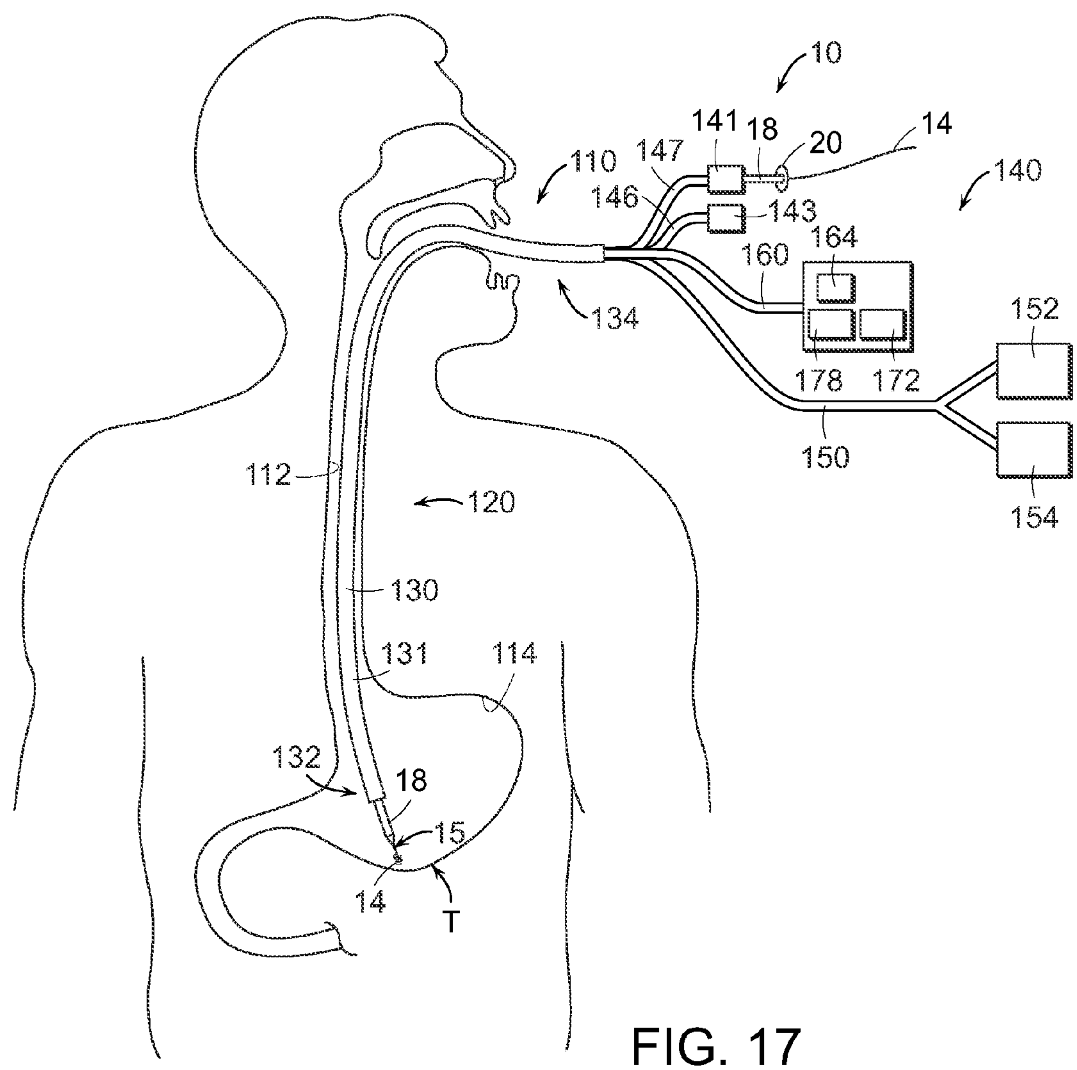

FIG. 17 illustrates one embodiment of the surgical device of FIG. 1 being used in conjunction with an overtube, an endoscope, and various other components and inserted into the upper gastrointestinal tract of a patient.

Figure 18:
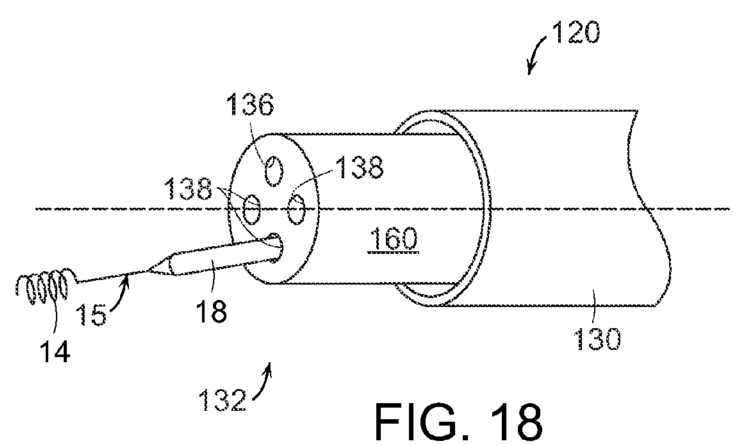

FIG. 18 illustrates a perspective view of the distal portion of one embodiment of the surgical device of FIG. 1 extending from a working channel of a distal end of the endoscope of FIG. 17.

DESCRIPTION

It will be appreciated that the terms "proximal" and "distal" are used herein with reference to a clinician, a surgeon, or a user ("surgeon") manipulating one end of an instrument or device that protrudes out of a patient (i.e., a natural orifice). The term "proximal" refers to a portion of the instrument or device closest to the surgeon and the term "distal" refers to a portion of the instrument located furthest from the surgeon. It will be further appreciated that for conciseness and clarity, spatial terms such as "vertical," "horizontal," "up," and "down" may be used herein with respect to the figures. Surgical instruments or devices, however, may be used in many orientations and positions and, as such, these terms are not intended to be limiting and absolute.

During the course of various surgical procedures, such as in intralumenal and translumenal access procedures, for example, there often exists a need to pierce the wall of hollow body organs or internal body lumens ("lumen" or "access lumen" hereinafter) with a needle to access a cavity, organ, or other lumen. From inside the lumen, a target exit is selected and after suctioning the target exit site of the lumen onto the distal end of an endoscope, using a distal tip of an over-the-scope overtube/endotrocar conduit, or an end cap, an elongated guide wire with a needle formed integrally at the distal end may be introduced through a conduit, such as a catheter, to the target exit site. The wall of the lumen may be pierced with a needle, a needle knife, or other cutting, piercing, incising, or puncturing member ("needle") in accordance with the described embodiments. In various embodiments, the needle may be solid or hollow such that the most distal end of the needle can puncture tissue. In one embodiment, the needle comprises an elongated member referred herein as a guide wire, a spiral, helical, or corkscrew shaped portion with a sharp metallic point or tip for piercing at a distal end ("helical portion" hereinafter), and in one embodiment, a tapered segment at the proximal end of the helical portion. Due to the nature of the helical portion, in one embodiment, the wall of the lumen may be pierced using a twisting motion (e.g., clockwise or counterclockwise) of the helical portion, of the needle, for example, which may be imparted by twisting the distal end of the guide wire, which extends outside the patient's body. The needle, including the guide wire, tapered segment, and helical portion, may be constructed of any suitable metals or alloys such as stainless steel, alloys of stainless steel, shape memory alloys such as nickel titanium (NiTi) commercially known as NITINOL, or any other materials suitable for piercing the walls of hollow organs or lumens.

As previously discussed, in one embodiment, a portion or segment of the elongated guide wire portion of the needle proximal to the helical portion may be tapered (necked down) to a smaller diameter to reduce the column strength of the guide wire, limiting the likelihood of damage to unintended anatomical structures once the guide wire is advanced through a catheter (e.g., a flexible or rigid hollow tube or conduit). This may allow a length of the guide wire to be fed into the peritoneum, or other hollow body cavity or lumen, outside the access lumen and left in place as a future path for repeated ingress/egress with an endoscope. In other embodiments, the helical portion may be formed separately from the guide wire portion and attached thereto using any known attachment technique. Once the helical portion and the guide wire are attached or formed integrally on a distal end thereof, the entire assembly may be referred to as a "needle" and/or guide wire, for example.

Once the wall of the access lumen is pierced with the helical needle, an inflatable member, such as a medical balloon, for example, may be used to enlarge the opening or incision in the wall or other tissue ("opening") formed with the helical portion of the needle. The opening is enlarged to create surgical space for advancing overtubes and surgical instruments or devices and/or for allowing a surgeon to access the translumenal surgical site. These inflatable members are commercially available from Boston Scientific Corporation, C. R. Bard, Inc., and Cook Medical Inc., for example. The inflatable member is then pushed behind the helical needle and dilated to stretch the exit site in preparation for an over-the-scope overtube/endotrocar entry, providing an atraumatic ingress/egress path for the endoscope.

In various embodiments, an overtube comprising a hollow conduit, different from a guide tube or guide wire conduit, can be introduced into a natural opening in a patient's body. In one embodiment, a guide tube or guide wire conduit can be inserted into the overtube which has been inserted into the natural opening in the patient's body. In one embodiment, an endoscope can be inserted into the overtube through the proximal end of the overtube and extend through or near the distal end of the overtube. In such an embodiment, the conduit can be positioned within a working channel of the endoscope and can extend from a distal end thereof to allow the conduit and the needle to gain access to the tissue proximal to a surgical site or surgical access site.

In various embodiments, an inflatable member, such as a medical balloon, for example, can be attached to, positioned on, surround, or can be integrally formed on or with an outer surface of a distal portion of the guide wire conduit, for example, and can be introduced into the opening in the tissue created by advancing the needle distally through the tissue. The inflatable member can then be transitioned from an uninflated or a collapsed state to an inflated or an expanded state thereby radially or otherwise displacing side walls of the opening to create a larger opening or surgical space in the tissue such that the enlarged opening can receive a portion of the endoscope, a portion of the overtube, and/or portions of other surgical instruments or devices, for example, therethrough.

In various embodiments, an inflation conduit can surround a portion of a conduit and can extend from a fluid source to a proximal portion of the inflatable member such that the inflatable member can be expanded with fluid from the fluid source. In one embodiment, the inflation conduit can comprise an inner diameter or perimeter larger than the outer diameter or perimeter of the conduit to allow the fluid from the fluid source to flow or be pumped into and out of the inflatable member. The fluid from the fluid source can flow or be pumped through a void created between the outer diameter or perimeter of the conduit and the inner diameter or perimeter of the inflation conduit, for example. As such, a distal portion of the inflation conduit can be attached to and in fluid communication with the proximal portion of the inflatable member with a distal portion of the inflatable member sealed to a portion of the conduit or member positioned on the conduit such that the inflatable member can be inflated. In other various embodiments, the inflation conduit can be eliminated and end portions of the inflatable member can be sealed to the conduit. The conduit can be in fluid communication with the fluid source at its proximal portion and be in fluid communication with the inflatable member at its distal portion through an opening, aperture, slot, or perforation (not illustrated) in the conduit. As a result, the fluid from the fluid source can be flowed or pumped into the conduit and through the opening, aperture, slot, or perforation, which can be in fluid communication with an internal area of the inflatable member to inflate the inflatable member.

Because the inflatable member is made of a very thin material, such as polyethylene terephthalate glycol, polyurethane, plastic, nylon, or combinations thereof, for example, it can be somewhat susceptible to tearing or puncturing while it is being fed through the overtube, the working channel of the endoscope, and while it is being advanced through the opening in the tissue. Further, the inflatable member can sometimes at least partially inflate prior to being positioned within the opening in the tissue owing to subatmospheric pressure conditions within the overtube. These subatmospheric pressure conditions can cause the inflatable member to prematurely inflate if the inflatable member is in fluid communication with atmospheric pressure or with a space having a higher pressure than the subatmospheric pressure conditions within the overtube. Even if a valve is supplied between the inflatable member and an atmospheric pressure space external to the patient, any fluid within the conduit and/or the inflation conduit may cause the inflatable member to at least partially inflate owing to the fluid remaining within the conduit and/or the inflation conduit intermediate the valve and the inflatable member. Such premature inflation can cause delays during a surgical procedure as a partially inflated inflatable member may not fit properly into the opening in the tissue. To at least partially alleviate or eliminate the above-referenced difficulties, a surgical device is provided with a protective sleeve which can, in some circumstances, at least partially cover the inflatable member at appropriate times during a surgical procedure to prevent, inhibit, or at least minimize opportunities for tearing, puncturing, or premature inflation of the inflatable member. The protective sleeve also may be provided to protect the endoscope channel from sharp points, and to keep the inflatable member properly pleated during initial insertion as described in accordance with the disclosed embodiments.

With reference now to FIGS. 1-5, illustrates a one embodiment of a surgical device 10 comprising a needle 5, an elongated guide tube 13, a conduit 11, an inflation conduit 12, and an inflatable member 16 covered by a protective sleeve 18 in an extended or a first position. A distal end 9 of the surgical device 10 comprises, the needle 5 comprises a helical element 14, a tapered element 15 located proximally relative to the helical element 14, and an elongated portion that is accessible at a proximal end 7 of the surgical device 10. In the embodiment, illustrated in FIGS. 3 and 5, the inflatable member 16 comprises a plurality of longitudinal pleats 35. The inflatable member 16 is disposed on an outside surface of the conduit 11, is in fluid communication with the inflation conduit 12, and is slidably received within the protective sleeve 18, to keep the inflatable member 16 properly pleated during initial insertion. In one embodiment, the surgical device 10 can be inserted into and extend through a distal end of a working channel of an endoscope positioned within an overtube, as described in further detail below. In various embodiments, the surgical device 10, via its various components such as the helical element 14, can be used to puncture tissue to create an opening therein and then expand the opening using the inflatable member 16, such that an overtube, the endoscope, and/or another surgical instrument or device can be advanced distally through the opening to gain access to a surgical site.

Figure 2:
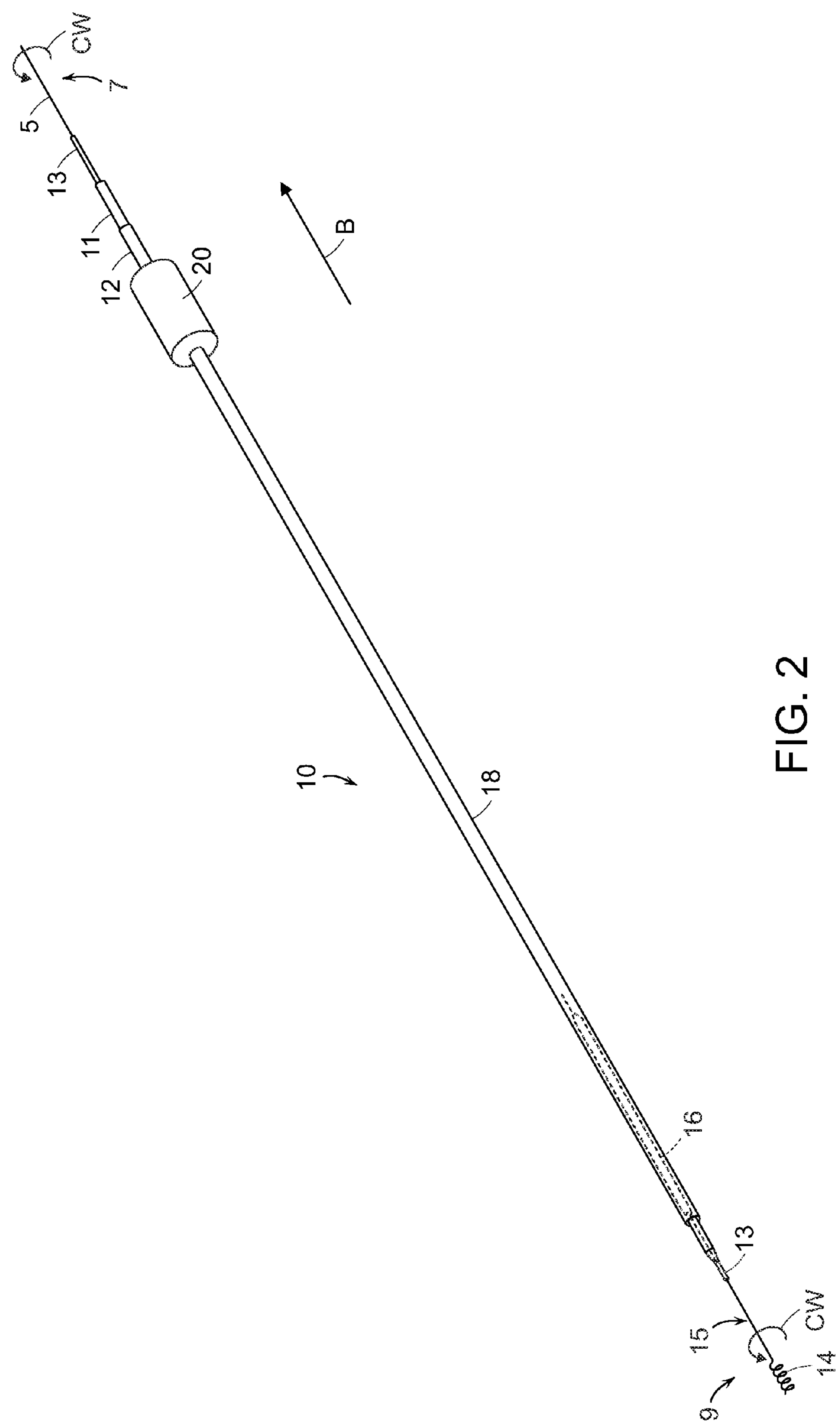
FIG. 2 illustrates a perspective view of one embodiment of the surgical device of FIG. 1 with the protective sleeve shown partially retracted to expose the needle and a tapered segment.
Figure 3:
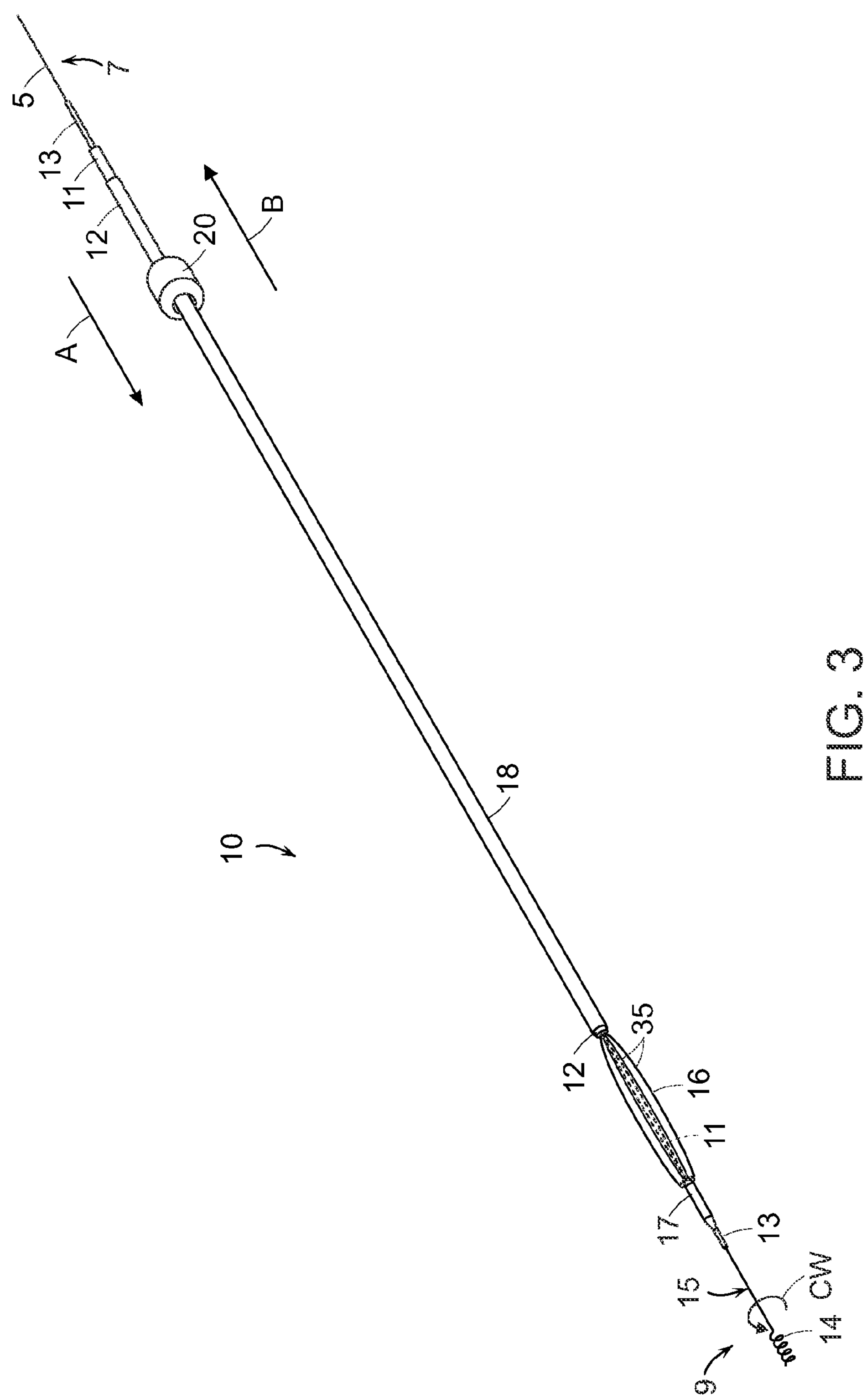
FIG. 3 illustrates a perspective view of one embodiment of the surgical device of FIG. 1 with the protective sleeve shown retracted to a second position to expose the needle, the tapered segment, and the inflatable member.
Figure 4:
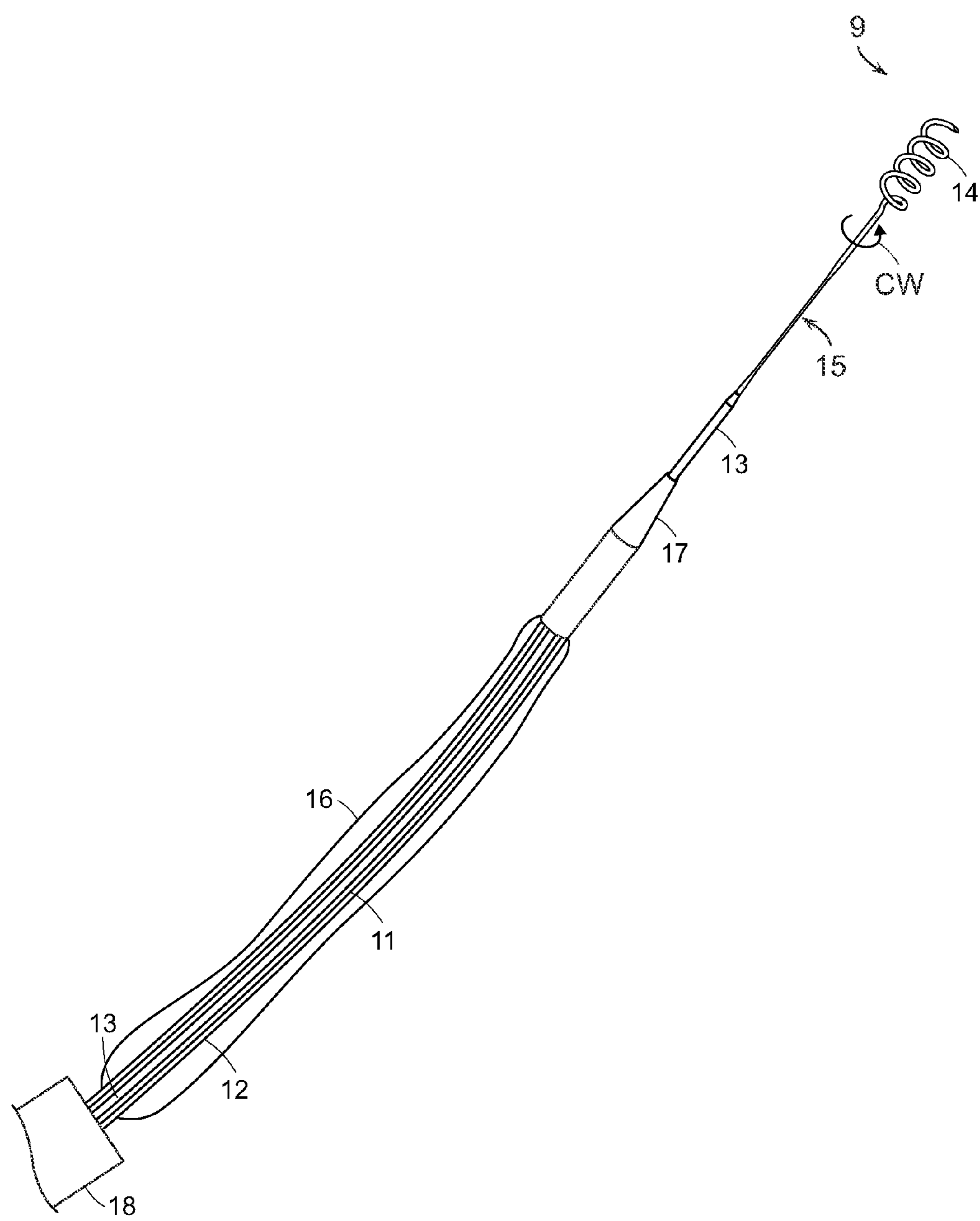
FIG. 4 illustrates an exploded view of one embodiment of an inflatable member of the surgical device of FIG. 1.

The protective sleeve 18 optionally comprises a handle or handle 20 on its proximal portion to slidably located the protective sleeve 18 in one or more desired positions. The protective sleeve 18 is configured to be positioned at least partially over (i.e., cover) the helical element 14 and the inflatable member 16 to protect and shield the inflatable member 16 from tearing, puncturing, and/or premature inflation, for example, and to prevent or minimize opportunities for the helical element 14 to puncture undesired tissue or damage any of the instruments during deployment. As previously discussed, the protective sleeve 18 keeps the inflatable member 16 properly pleated during initial insertion. Using the handle 20, a clinician can be push the protective sleeve 18 distally in the direction indicated by arrow "A" to deploy the protective sleeve 18 as shown in FIG. 1. The protective sleeve 18 can be pulled proximally in the direction indicated by arrow "B" to expose the distal end 9 of the needle 5, the helical element 14 and the tapered element 15, as shown in FIG. 2, where the protective sleeve 18 is in a partially retracted first position exposing the helical element 14 and the tapered element 15. The protective sleeve 18 can be pulled proximally further in the direction indicated by arrow "B" to also expose inflatable member 16, as shown in FIGS. 3 and 4, for example, where the protective sleeve 18 is shown in a further retracted second position exposing the helical element 14, the tapered element 15, and the inflatable member 16.

In various embodiments, the needle 5 may be formed in a variety of configurations. In one embodiment, the helical element 14, the tapered element 15, and the elongated portion of the needle may be formed integrally or as separate attachable elements. For example, the helical element 14 may be attachable to the tapered element 15, which may be attachable to the elongated portion of the needle 5. These elements may be attached using any suitable techniques, such as, for example, bolting, screwing, welding, crimping, gluing, epoxying, bonding, brazing, soldering, press fitting, snap fitting, riveting, heat shrinking, ultrasonic welding or any other suitable method. In other embodiments, the helical element 14 and/or the tapered element 15 may be attached to the distal end of the guide tube 13, thus eliminating the need for the elongated portion of the needle 5. In this respect, the terms guide tube 13 and needle 5 may be used interchangeably and the guide tube 13 may take the form of a solid or stranded wire and hence may be referred to as a guide wire, without limitation. In other embodiments, the helical element 14 and/or the tapered element 15 may be formed integrally on a distal end of the guide tube 13. Therefore, the term "needle" may encompass the guide tube 13 with an attached helical element 14 and/or tapered element 15 or the guide tube 13 with an integrally formed helical element 14 and/or tapered element 15, without limitation.

The helical element 14 portion of the needle 5 may be employed to penetrate, pierce, cut, incise, grasp, or puncture tissue in accordance with the described embodiments. In one embodiment, the helical element 14 comprises a spiral, helical, or corkscrew ("helical" hereinafter) shape with a sharp metallic point or tip at the distal end that is suitable for penetrating tissue. The helical element 14 can be formed with a wire or tube having an outside diameter suitable for penetrating, piercing, cutting, incising, grasping, or puncturing tissue. Accordingly, the wall of an internal body lumen may be pierced using a twisting motion of the helical element 14, for example. In the illustrated embodiment, an internal body lumen may be pierced by threading or twisting the helical element 14 in a clockwise direction as illustrated by arrow "CW," in FIGS. 2-4, for example. In other embodiments, however, to pierce the lumen the helical element 14 may be threaded or twisted in a counterclockwise direction. Once an initial opening is formed in the lumen using the helical element 14, the tapered element 15 portion and the guide tube 13 may be fed into the peritoneum, or other hollow body cavity or lumen, outside the access lumen, and left in place as a future path for repeated ingress/egress with an endoscope. The helical element 14 may be constructed of any suitable metals or alloys such as stainless steel, alloys of stainless steel, shape memory alloys such as nickel titanium (NiTi) commercially known as NITINOL, or any other materials suitable for piercing the walls of hollow organs or lumens. When formed of a shape memory alloy, the helical element 14 may be pulled in direction "B" through the opening defined by the guide tube 13.

Figure 5:
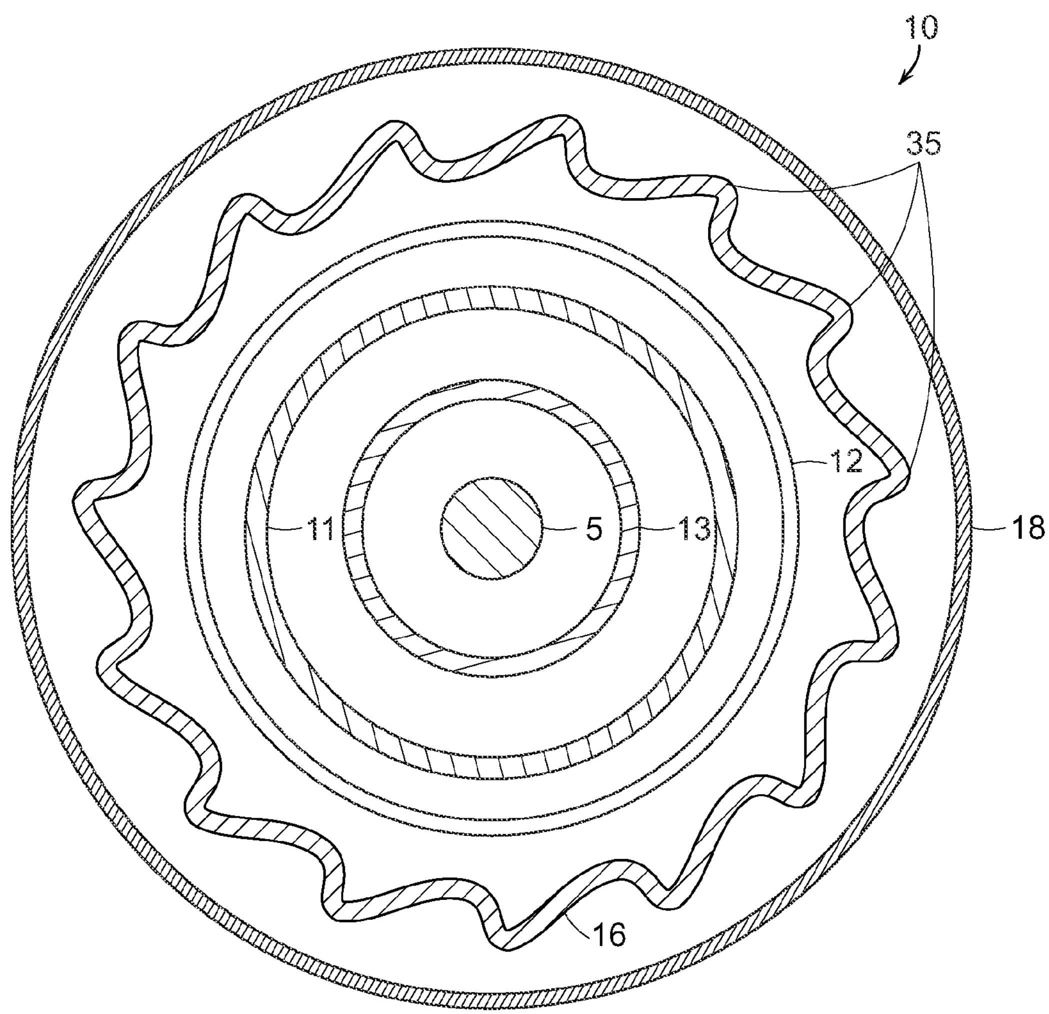
FIG. 5 illustrates a cross-sectional view of one embodiment of the surgical device taken along line 5-5 of FIG. 1.

For additional clarity, FIG. 5 illustrates a cross-sectional view of the embodiment of the surgical device 10 taken along line 5-5 of FIG. 1 to illustrate the relative positions of the protective sleeve 18, the inflation conduit 12, the conduit 11, the guide tube 13, and the needle 5 and one embodiment of how these elements can be situated. The protective sleeve 18 can have an inner diameter or perimeter which is larger than a respective outer diameter or perimeter of the inflatable inflation conduit 12, the conduit 11, and the inflatable member 16 to enable the protective sleeve 18 to at least partially or fully surround a portion of the inflatable inflation conduit 12 and/or the inflatable member 16.

Figure 6:
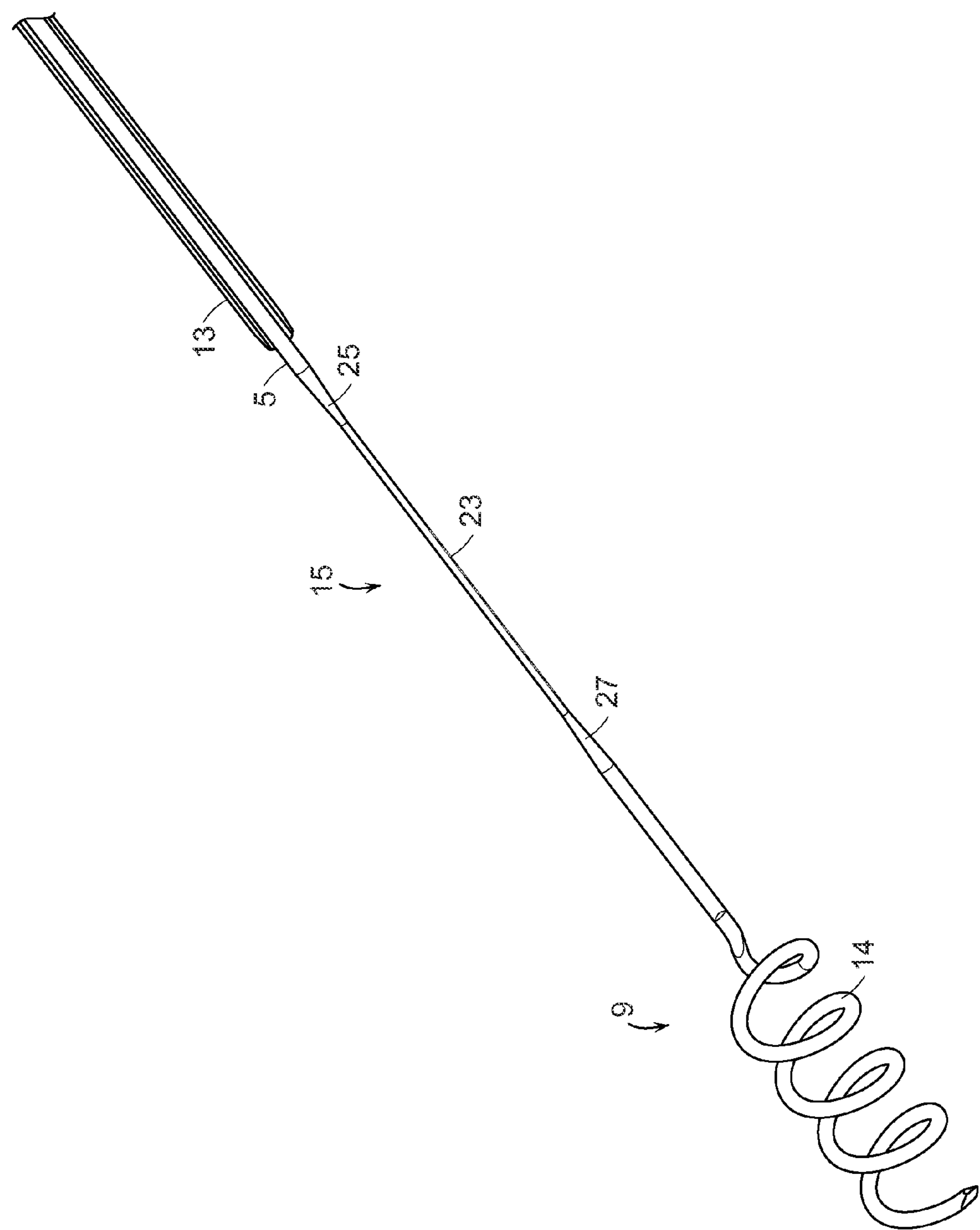
FIG. 6 is a perspective view of a distal portion of one embodiment of a needle of the surgical device of FIG. 1 showing a partial cross-sectional view of a guide tube to receive the needle.

An enlarged view of the tapered element 15 is shown in FIG. 6. In one embodiment, a distal portion of the needle 5 proximal the helical element 14 may be tapered (necked down) to a smaller diameter to define the tapered element 15. The tapered element 15 comprises a middle segment 23 having a diameter $d_1$ that is less than the outside diameter $d_1$ of the elongated portion of the needle 5. A first tapered segment 25 reduces the outside diameter $OD_5$ of the needle 5 to the diameter $d_2$ of the middle segment 23 and a second tapered segment 27 reduces the diameter $d_3$ of the helical element 14 to the diameter $d_2$ of the middle segment 23. In one embodiment the diameter $d_1$ of the needle 5 is substantially the same as the diameter $d_3$ of the helical element 14, however, in other embodiments the diameters $d_1$ and $d_3$ may be different. The middle segment 23 portion of the tapered element 15 makes middle segment 23 slightly bendable or collapsible under an applied longitudinal force, which may result when pushing on the needle 5 in direction "A," for example. Thus, the tapered element 15 reduces the column strength of the needle 5 to minimize or limit the likelihood of unintentionally damaging anatomical structures when the needle 5 is advanced translumenally through layers of tissue. The bendability or collapsibility of the tapered segment 23 prevents a build up of pressure against the tissue to be pierced and allows a more controlled advancement of the distal portion of the needle 5 though the tissue.

Figure 7:
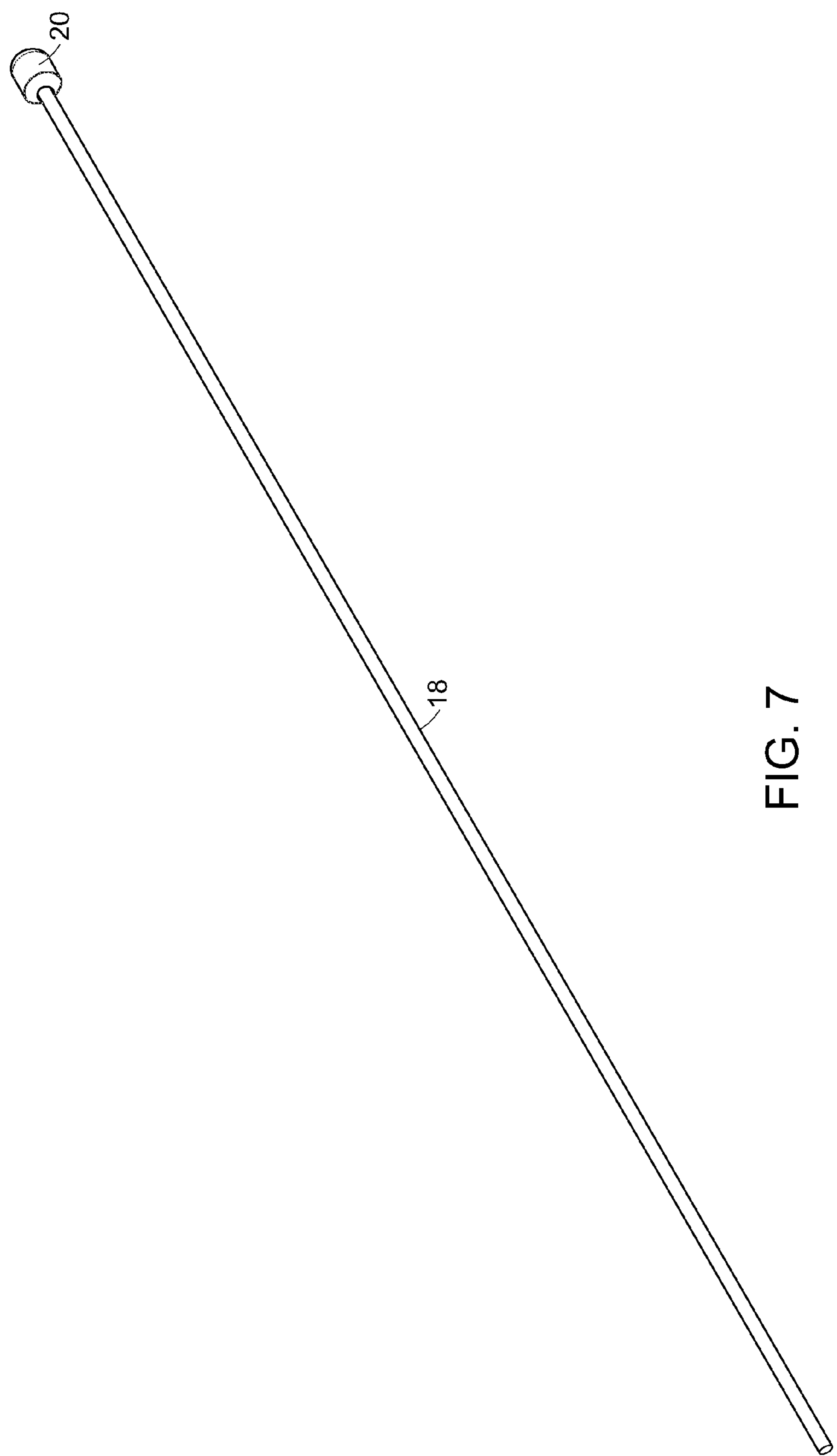
FIG. 7 illustrates a perspective view of one embodiment of a protective sleeve for the surgical device of FIG. 1.
Figure 8:
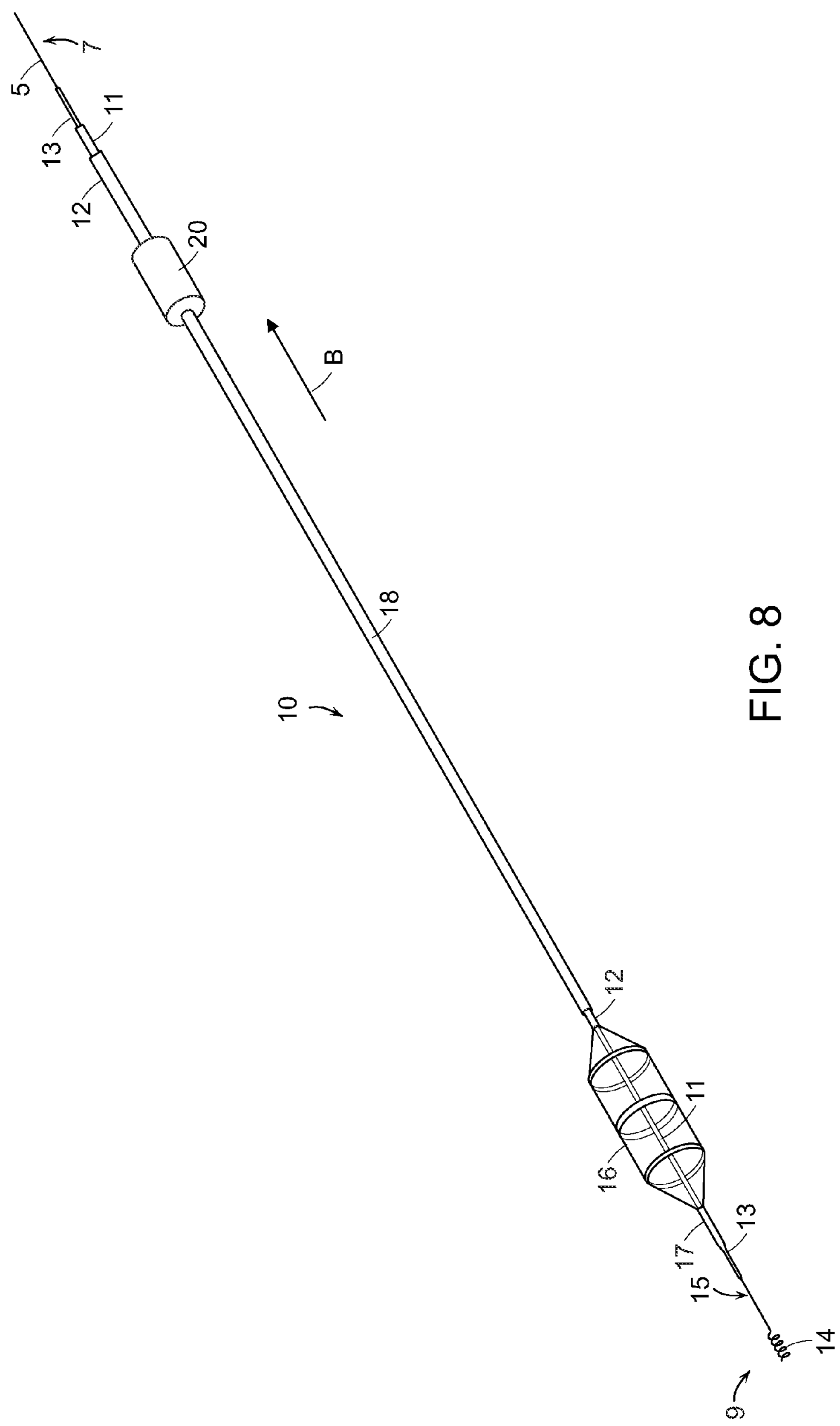
FIG. 8 illustrates a perspective view of one embodiment of the surgical device of FIG. 1 showing a protective sleeve in a retracted or second position exposing the needle, the tapered segment, and the inflatable member in an inflated state.

FIG. 7 illustrates a perspective view of the embodiment of the protective sleeve 18 of the surgical device of FIG. 1. As previously discussed, the protective sleeve 18 can be movable by way of the handle 20, for example, between the first position (see e.g., FIG. 1), to cover, or at least partially cover, the helical element 14, the tapered element 15, and the inflatable member 16, and a second position (see e.g., FIG. 3), where it can expose the helical element 14, the tapered element 15, and the inflatable member 16 for inflation. In one embodiment, using the handle 20, a clinician (e.g., surgeon) can slide the protective sleeve 18 between the first position and the second position (or into any other suitable intermediate position) by applying a proximal-to-distal force, in direction A (i.e., pushing, as shown in FIGS. 1 and 3), or by applying a distal-to-proximal force, in direction B (i.e., pulling, as shown in FIGS. 2 and 3). The optional handle 20 may be integrally formed with or on or attached to a proximal portion of the protective sleeve 18 to facilitate slidable movement of the protective sleeve 18 relative to the inflation conduit 12. It will be appreciated by those of ordinary skill in the art that any suitable handle or gripping device can be used with the surgical device 10. Further, the handle 20 can be eliminated and the surgeon can instead grasp the proximal portion of the protective sleeve 18 to move the protective sleeve 18 between the first and the second positions and any other suitable positions. In one embodiment, the protective sleeve 18 may be frictionally coupled or engaged to the inflation conduit 12 in any suitable manner. It will be appreciated by those of ordinary skill in the art that any other suitable mechanical members can be used to advanced and/or retract the protective sleeve 18 relative to the inflation conduit 12. In other various embodiments, the advancement and retraction of the protective sleeve 18 can be automated through the use of at least one actuator, for example.

In one embodiment, the protective sleeve 18 and the handle 20 may be attached using any suitable techniques, such as, for example, bolting, screwing, welding, crimping, gluing, epoxying, bonding, brazing, soldering, press fitting, snap fitting, riveting, heat shrinking, ultrasonic welding or any other suitable method. In one embodiment, the protective sleeve 18 and the handle 20 may be threadably connected, for example. The handle 20 can have female threads formed on an inner surface thereof and the protective sleeve 18 can have male threads formed on an outer surface thereof such that the threads on the outer surface of the protective sleeve 18 engage the threads on the inner surface of the handle 20. In another embodiment, the protective sleeve 18 and the inflation conduit 12 may be threadably connected, for example. The inflation conduit 12 can have male threads formed on an outer surface thereof and the protective sleeve 18 can have female threads formed on an inner surface thereof such that the threads on the inner surface of the protective sleeve 18 engage the threads on the outer surface of the inflation conduit 12.

With reference now to FIGS. 1-7, generally, the inflation conduit 12 may define a longitudinal opening therethrough long enough to extend from a proximal end of the inflatable member 16 to a proximal end 7 of the surgical device 10. The inflation conduit 12 may be formed of or may comprise a flexible material to allow at least its distal portion to travel through the tortuous path within the patient's body to and at least partially through the opening in the tissue. In one embodiment, the needle 5 can be sized and configured to be slidably disposed within the guide tube 13. The guide tube 13 and the needle 5 may sized and configured to be slidably disposed within the conduit 11, which extends from a distal portion of the inflatable member 16 to a proximal end 7 of the surgical device 10.

In one embodiment, the various components of the surgical device 10 may have the following dimensions selected such that the various internal components are slidably movable within certain defined openings of the external components. Accordingly, in one embodiment, the protective sleeve 18 has an inside diameter $ID_1$ of about 2.4 mm and an outside diameter $OD_1$ of about 2.6 mm. The outside diameter $OD_1$ of the protective sleeve 18 is selected such that it is slidably movable within a typical working channel of an endoscope, which typically may vary from about 2.8 mm to about 3.7 mm. The inflation conduit 12 has an inside diameter $ID_2$ of about 1.8 mm and an outside diameter $OD_2$ of about 2.3 mm. The outside diameter $OD_2$ of the inflation conduit 12 is less than the inside diameter $ID_1$ of the protective sleeve 18 such that the protective sleeve 18 can slidably move over the inflation conduit 12. The conduit 11 has an outside diameter $OD_3$ of about 1.5 mm and an inside diameter $ID_3$ of about 1.0 mm. The outside diameter $OD_3$ of the conduit 11 is less than an inside diameter $ID_2$ of the inflation conduit 12 such that the conduit 11 can be slidably received within the longitudinal opening defined by the inflation conduit 12. The guide tube 13 has an outside diameter $OD_4$ of about 0.9 mm and an inside diameter $ID_4$ of about 0.7 mm, which is less than the inside diameter $ID_3$ of the conduit 11 such that the guide tube 13 can slidably move within the conduit 11. The needle 5 has an outside diameter $OD_5$ ranging from about 0.4 mm to about 0.5 mm, which is less than the inside diameter $ID_4$ of the guide tube 13 such that the needle 5 is slidably movable within the longitudinal opening defined by the guide tube 13. In one embodiment, the inflation conduit 12 and the conduit 11 are fixed and the needle 5 is configured to be slidably movable within the longitudinal opening defined by the guide tube 13. In another embodiment, the guide tube 13 may be slidably movable within the longitudinal opening defined by the conduit 11 and/or the inflation conduit 12. These dimensions are provided merely as examples and are not limited in this context.

In various embodiments, apertures, cut-outs, slots, and/or joints (not shown) may be formed on the protective sleeve 18 to make the device lighter and/or for various surgical reasons, such as, for example, to add flexibility to the protective sleeve 18 and/or to facilitate the steerability of the protective sleeve 18. Also, the protective sleeve 18 can be formed of or comprise a transparent or semi-transparent material. In one embodiment, the protective sleeve 18 may be formed of or may comprise a lubricious, low coefficient of friction material, such as polyethylene, polyetheretherketone (PEEK®), polytetrafluoroethylene (TEFLON®), plastic, nylon, ethylene, and/or a combination thereof, for example, to enable easy sliding movement of the protective sleeve 18 over the inflation conduit 12 and/or the inflatable member 16. In such an embodiment, the lubricious, low coefficient material can also help prevent, inhibit, or at least minimize any opportunities for the protective sleeve 18 from tearing or puncturing the inflatable member 16 when sliding over the inflatable member 16 and/or when sliding between the first position and the second position. In various embodiments, the protective sleeve 18 can be flexible as required for traveling along the tortuous path inside the patient's body to the surgical site. In other various embodiments, portions of the protective sleeve 18 can be flexible while other portions can be rigid or semi-rigid, for example. As previously discussed, the protective sleeve 18 may comprise additional features to enhance its flexibility and/or steerability.

With reference now to FIGS. 8-11, the surgical device 10 is shown with the protective sleeve 18 in a retracted or second position and the inflatable member 16 exposed and inflated through the use of a fluid source 22 (e.g., liquid or gas). In the embodiment illustrated in FIGS. 8-11, the inflatable member 16 is in fluid communication with the fluid source 22, which is configured to supply a fluid for filling or inflating the inflatable member 16 at an appropriate time during the surgical procedure. The fluid source 22 can be in fluid communication with the inflatable member 16 through the inflation conduit 12. In one embodiment, fluid source 22 can be in fluid communication with the inflatable member 16 through a tube 21 connecting the fluid source 22 and the inflatable member 16 through the inflation conduit 12. The fluid source 22 can be in fluid communication with the inflatable member 16 through the inflation conduit 12 and an optional tube 21 connecting the fluid source 22 and the inflation conduit 12. A proximal handle 29 (FIG. 11) may be provided to apply a torque to the guide tube 13.

As previously discussed, the inflation conduit 12 can extend at least from the proximal portion of the inflatable member 16 to the tube 21 (or the inflatable member 12 can extend directly to the fluid source 22) and can have an inner diameter or perimeter larger than the outer diameter or perimeter of the conduit 11. As such, a void can be formed intermediate the inner surface of the inflation conduit 12 and the outer surface of the conduit 11. The inflatable member 16 can also be sealed with the conduit 11 or other member on the conduit 11 at its distal portion and can be in fluid communication with the inflation conduit 12 on its proximal portion such that the inflatable member 16 can be inflated by the fluid source 22. The fluid from the fluid source 22 can then be flowed or pumped through the tube 21, through the void, and then into the inflatable member 16. In one embodiment, the inflatable member 16 may be inflated by controlling a control unit (not illustrated) external to the patient that can be operated by the surgeon. In other embodiments, the inflatable member 16 may be inflated by the surgeon activating a manual pump or another suitable inflation device, for example.

In various embodiments, the inflatable member 16 can be filled with a fluid, in liquid or gas form, such as saline or carbon dioxide, for example, as such fluids are common to the patient's body and can be easily absorbed and/or exhausted by the body. In various embodiments, as the inflatable member 16 is filled with the fluid, the inflatable member 16 can expand radially outward from the inflation conduit 12 to enlarge the size of the opening in the tissue. It will be appreciated that the inflatable member 16 can expand in any suitable fashion depending on the configuration of the inflatable member 16 and the particular surgical need.

Figure 9:
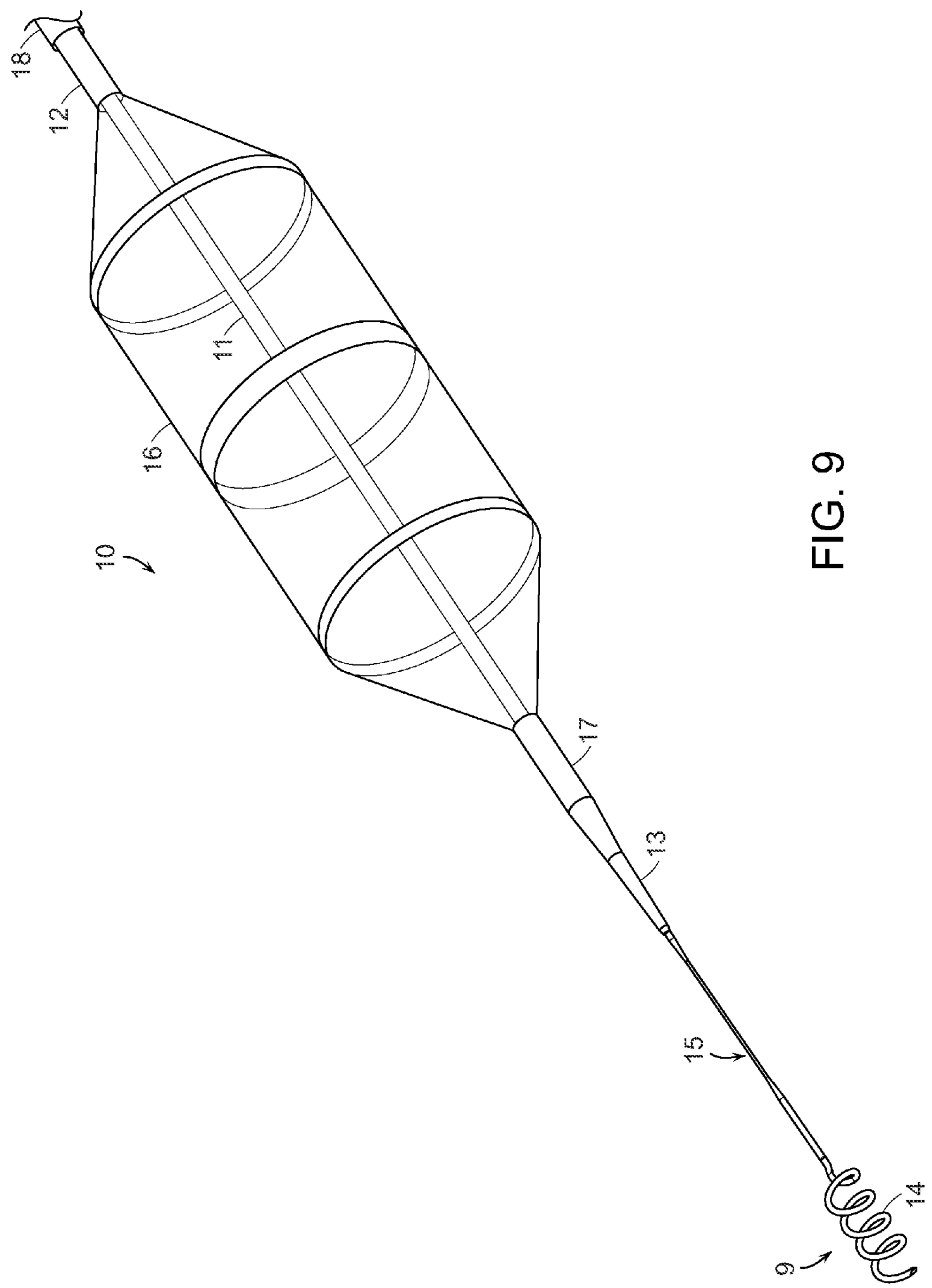
FIG. 9 illustrates a perspective close-up view of one embodiment of the surgical device of FIG. 1 showing a close-up view of a distal end of the surgical device showing the protective sleeve in a retracted or second position exposing the needle, the tapered segment, and the inflatable member with the inflatable member in an inflated state.
Figure 10:
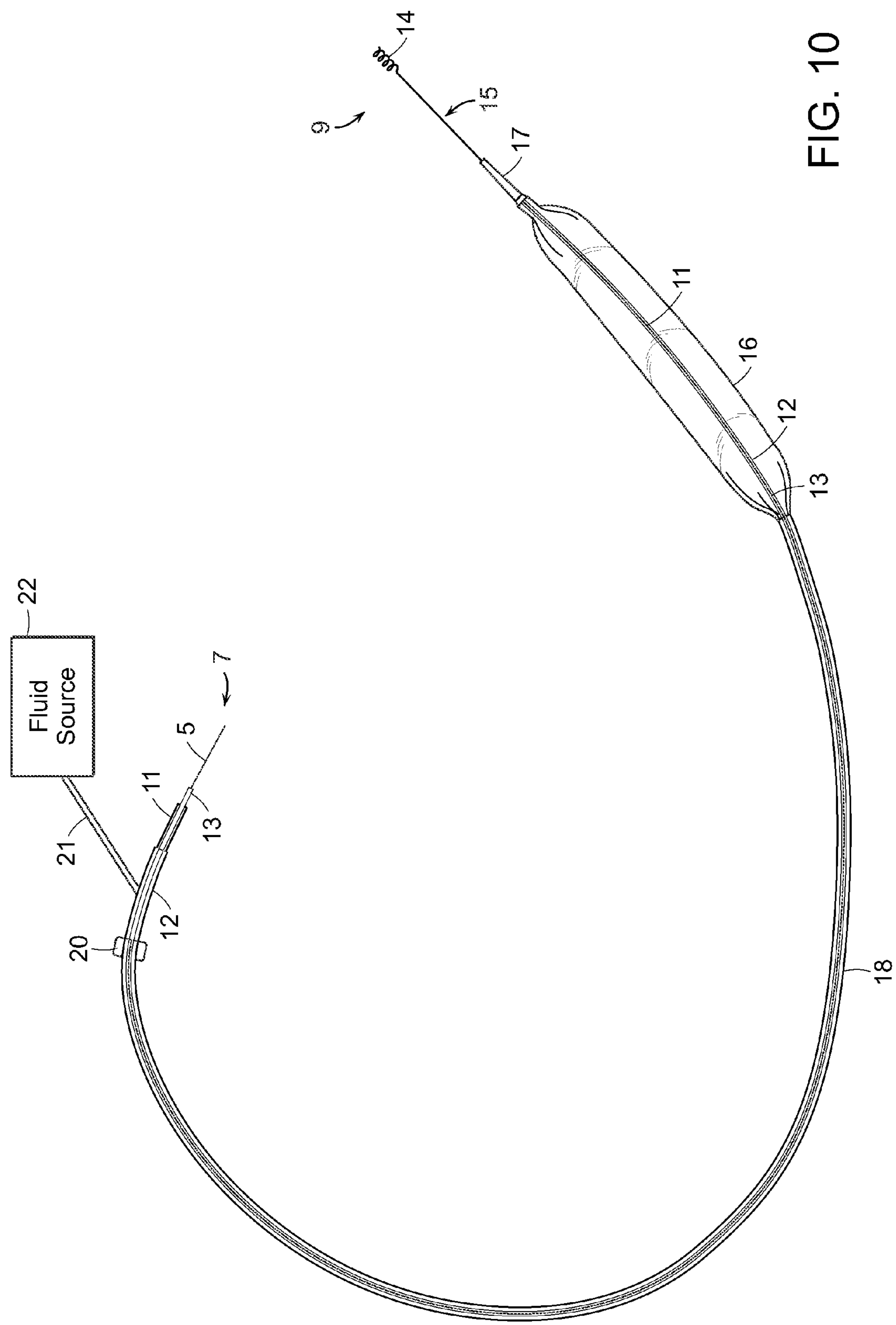
FIG. 10 illustrates a perspective close-up view of one embodiment of the surgical device of FIG. 1 in fluid communication with a fluid source showing the protective sleeve in a retracted or second position exposing the needle, the tapered segment, and the inflatable member with the inflatable member in an inflated state.
Figure 11:
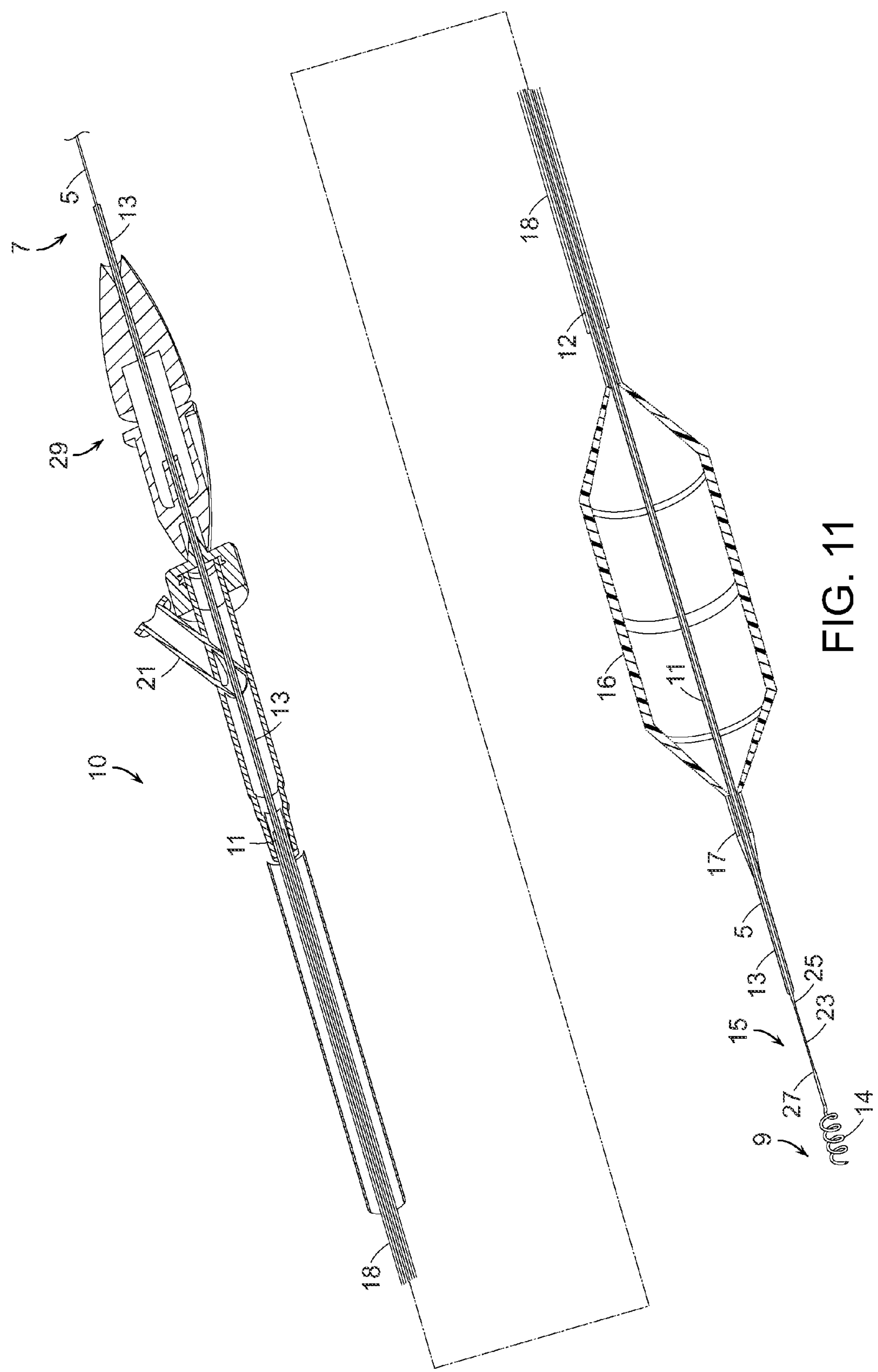
FIG. 11 is a cross-sectional view of one embodiment of the surgical device of FIG. 1.

As shown in more detail in FIG. 9, the conduit 11 may be disposed within the inflation conduit 12. The conduit 11 provides a channel for the guide tube 13. The conduit 11 is attached to the distal end of the inflatable member 16 and extends therefrom to the proximal end 7 of the surgical device 10. The inflation conduit 12 is attached to the proximal end of the inflatable member 16 and extends therefrom to the proximal end 7 of the surgical device 10. The proximal end of the inflatable member 16 is in fluid communication with the inflation conduit 12 and the inflation source 22. The distal end of the inflatable member 16 is sealed between the outside diameter surface of the conduit 11 and the inside diameter surface of a tapered tip 17.

In various embodiments, the proximal end of the inflatable member 16 can be integrally formed with, integrally formed on, positioned on, or attached to an outer surface of the distal portion of the inflation conduit 12. In various embodiments, the proximal end of the inflatable member 16 partially surrounds the distal portion of the inflation conduit 12. As the inflatable member 16 can surround the distal portion of the inflation conduit 12, it may have a larger, or slightly larger, outer perimeter or diameter than the outer perimeter or diameter of the inflation conduit 12 in its uninflated state. Likewise, as the inflation conduit 12 can surround a portion of the conduit 11, it can have a larger, or slightly larger, outer perimeter or diameter than the outer perimeter or diameter of the conduit 11. It will be appreciated that more than one inflatable member can be used with the surgical device 10 as is recognized by those of ordinary skill in the art. Further, the inflatable member 16 may comprise any suitable inflatable member known to those of ordinary skill in the art.

FIGS. 12-16 illustrate the surgical device 10 at various stages of deployment through a cross-section of tissue 32. In use, the surgical device 10 can be configured to be slidably received within an overtube 24 and an endoscope 26 comprising at least one working channel 28. The endoscope 26 can be any suitable endoscope known to those of ordinary skill in the art. In various embodiments, the overtube 24 can first be inserted into a natural orifice of a patient's body. In at least one embodiment, the endoscope 26 can then be positioned within and extend at least partially through the overtube 24 or extend to or from a distal end 30 of the overtube 24. In at least one embodiment, the distal end 30 of the overtube 24 can engage the tissue 32 and can apply suction to the tissue 32 owing to the subatmospheric pressure conditions created within the overtube 24. The overtube 24 can be in fluid communication with any suitable suction source such as a vacuum pump, for example, (not illustrated) or other suitable vacuum producing device. Appropriate end seals (not illustrated) may be provided to maintain the subatmospheric pressure conditions within the overtube 24. These subatmospheric pressure conditions within the overtube 24 can cause a portion of the tissue 32 proximal to a surgical access site to be pulled or drawn into the overtube 24 to locate the tissue 32 for puncturing with the helical element 14 of the guide tube 13 of the surgical device 10. The suction applied to the tissue 32 at the distal end 30 of the overtube 24 can at least partially offset any proximal-to-distal (i.e., pushing) force, in direction "A" (as shown in FIGS. 1 and 3), being applied to the tissue 32. The helical element 14 of the needle 5 is advanced until it contacts the tissue 32. As previously discussed, the tissue 32 may be pierced by threading the helical element 14 in a clockwise rotation "CW."

As previously referenced, if the proximal end of the inflation conduit 12 and/or the conduit 11 is open to atmospheric pressure (i.e., not sealed), or even if the inflation conduit 12 and/or the conduit 11 has a valve at its proximal end, the inflatable member 16 could still, at least partially, prematurely inflate owing to the subatmospheric pressure conditions within the overtube 24. As previously discussed, premature inflation of the inflatable member 16 can cause the inflatable member 16 to be enlarged such that it may not fit within the opening in the tissue 32. To address this issue, the protective sleeve 18 may be located in the first position to prevent, inhibit, or at least minimize such premature inflation from occurring by containing the inflatable member 16 within the inflation conduit 12 and thus inhibiting, for example, the inflatable member from expanding outwardly relative to the inflation conduit 12 and/or the conduit 11 prior to an appropriate time during a surgical procedure. Stated another way, the protective sleeve 18 can surround the inflatable member 16 closely enough to at least inhibit the inflatable member 16 from prematurely inflating. Furthermore, to any extent that the inflatable member 16 may partially inflate due to the tolerances of manufacturing, the inflatable member 16 can be contained within the hollow elongate opening defined by the protective sleeve 18 and, thus, can be inhibited from inflation by the protective sleeve 18, for example.

Figure 12:
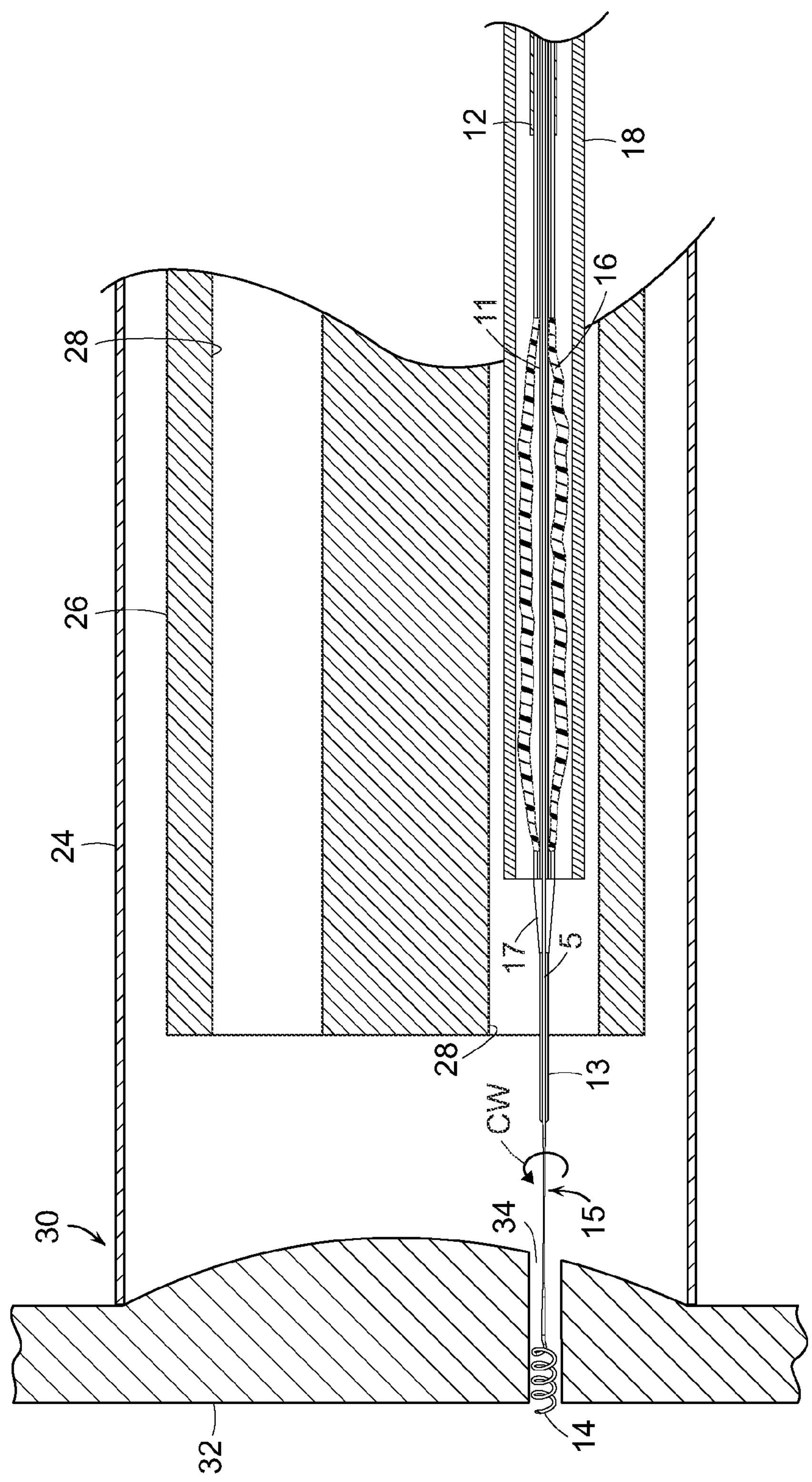
FIG. 12 illustrates a cross-sectional view of a distal portion of one embodiment of the surgical device of FIG. 1 extending through a working channel of an endoscope and creating an opening in tissue to allow access to a surgical site.
Figure 13:
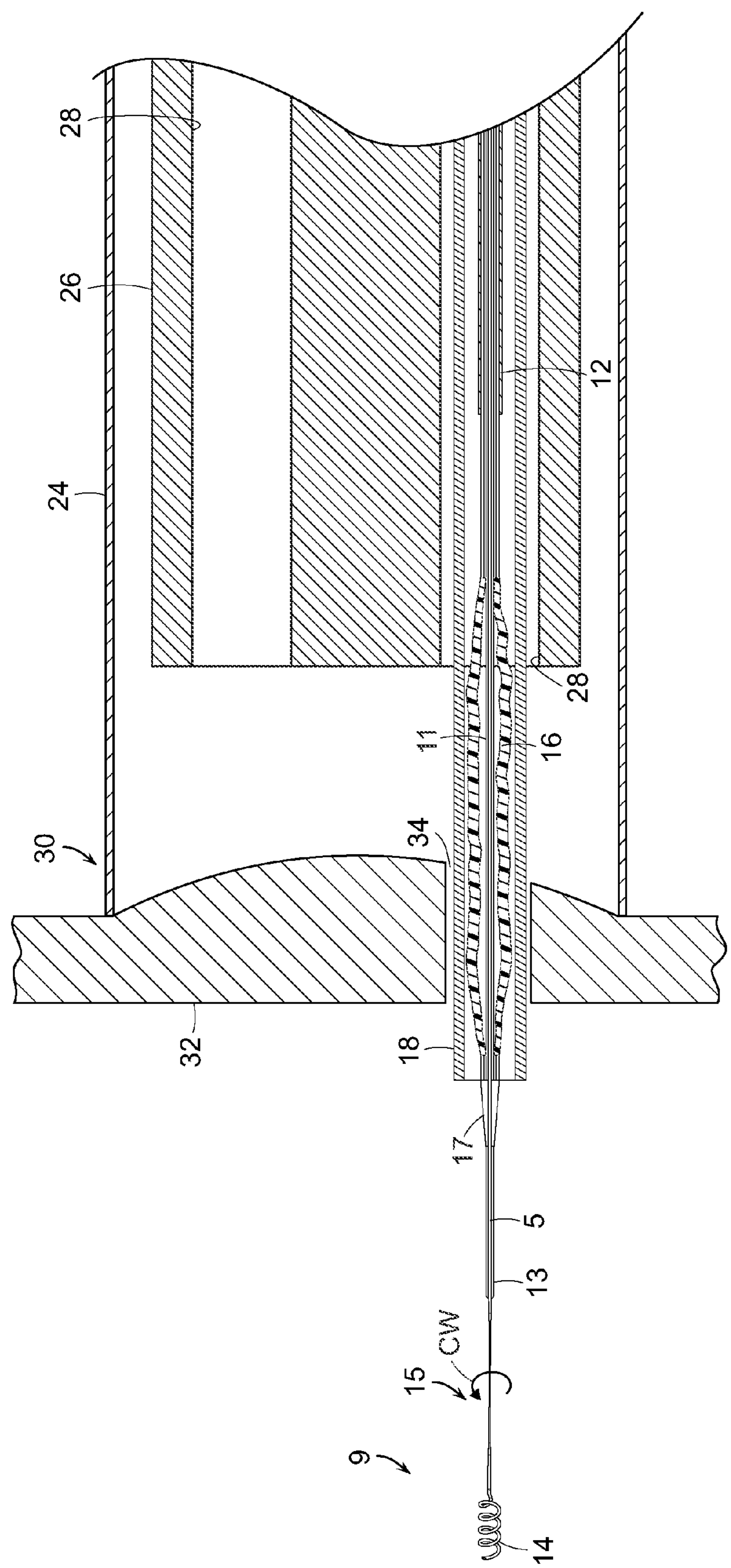
FIG. 13 illustrates a cross-sectional view of the distal portion of one embodiment of the surgical device of FIG. 1 with the protective sleeve in a first position and being advanced through the opening in the tissue.

With reference to FIGS. 12 and 13, while the suction is applied to the tissue 32, the helical element 14 is advanced into the tissue 32 by threading the helical element 14 in a clockwise rotation "CW" to puncture or pierce the tissue 32 and create an initial "helical needle sized" opening 34 therein. Once the helical element 14 has punctured or pierced through the tissue 32 and has created the opening 34, the distal end 9 of the surgical instrument is advanced through the opening 34. The tapered tip 17 at the distal end of the inflatable member 16 is then advanced through the opening 34, stretching it to advance the inflatable member 16 to a position within the opening 34. Owing to the position of the inflatable member 16 on or attachment to, for example, the distal portion of the inflation conduit 12 and the relative stretchability of the tissue 32, the inflatable member 16 can be advanced distally toward, into, and at least partially through the opening 34 in the tissue 32. This advancement can be accomplished by the surgeon applying a proximal-to-distal (i.e., pushing) force to the proximal portion of the inflation conduit 12 in direction "A." While advancing the inflation conduit 12, the protective sleeve 18 can also be advanced by the surgeon again applying a proximal-to-distal (i.e., pushing) force to the proximal portion of the protective sleeve 18 and/or to the handle 20, in direction "A," to maintain the inflatable member 16 in a shielded or protected state (i.e., the first position) until it is ready to be inflated.

FIG. 13 illustrates one stage of deployment of the surgical device 10 through the cross-section of tissue 32. As illustrated, the protective sleeve 18, along with the inflation conduit 12 and the inflatable member 16, can be advanced at least partially through the opening 34 in the tissue 32 with the protective sleeve 18 in the first position to cover the inflatable member 16. In this manner, the protective sleeve 18 shields the inflatable member 16 and protects it from puncturing or tearing during the advancement stage of deployment. The protective sleeve 18 generally should be advanced through the opening 34 in the tissue 32 while in the first position, although the inflation conduit 12 and the inflatable member 16 could be advanced through the opening 34 when the protective sleeve 18 is in the second position or in any other suitable intermediate position.

Figure 14:
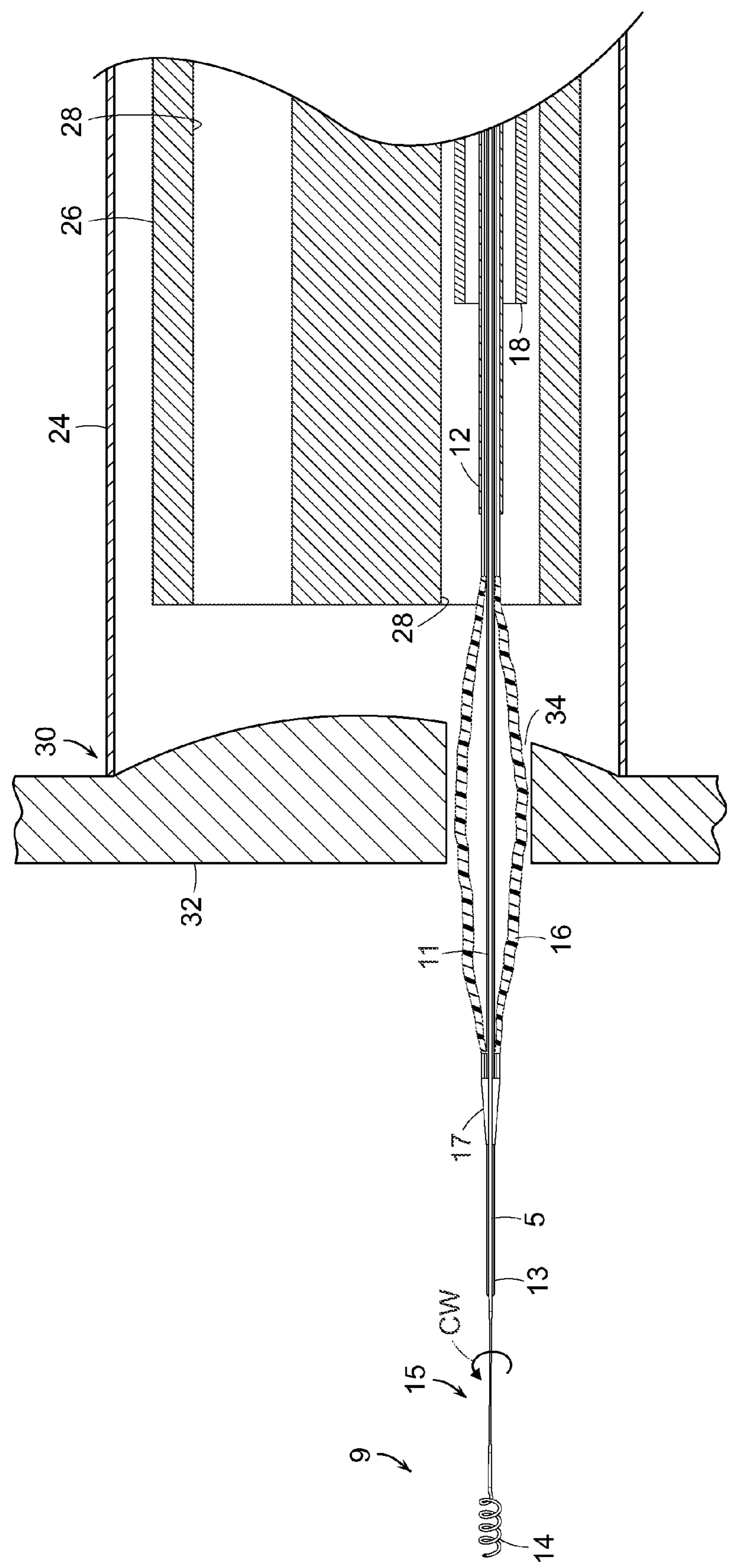
FIG. 14 illustrates a cross-sectional view of the distal portion of one embodiment of the surgical device of FIG. 1 after the protective sleeve has been retracted into the second position to expose the inflatable member to the opening in the tissue.

Referring to FIG. 14, once the protective sleeve 18, the inflation conduit 12, and the inflatable member 16 are advanced through the opening 34 in the tissue 32, the protective sleeve 18 can be retracted into the second position. This retraction can be accomplished by the surgeon applying a distal-to-proximal (i.e., pulling or retracting) force, in the direction “B,” to the proximal portion of the protective sleeve 18 and/or to the optional handle 20. As illustrated in FIG. 14, when the protective sleeve 18 is retracted into the second position, the inflatable member 16 can be exposed such that it can be inflated via the inflation conduit 12 and the fluid source 22 to expand the opening 34 in the tissue 32.

As shown in FIG. 15, before the inflatable member 16 is inflated, the distal end 30 of the overtube 24 can be partially withdrawn from contact with the tissue 32 to alleviate or eliminate the suction being applied to the tissue 32. Alternatively, the vacuum source could be powered off, for example, while maintaining the distal end 30 of the overtube 24 in contact with the tissue 32. The fluid source 22 (see FIG. 7) can then flow a fluid into the inflatable member 16 through the inflation conduit 12 to inflate the inflatable member 16. Alternatively, the conduit 11 may be configured such that the fluid can be flowed through the conduit 11 to inflate the inflatable member 16.

As shown in FIG. 15, as the inflatable member 16 is filled with the fluid, the inflatable member 16 can apply a force to the sidewalls 36 of the opening 34 created in the tissue 32 to radially or otherwise expand the opening 34 given the relatively elastic properties of the tissue 32. This expansion can continue until the opening 34 is large enough to accommodate the distal end 30 of the overtube 24 and/or the distal end of the endoscope 26 therethrough, for example. Once the opening 34 is expanded to a suitable size by the inflatable member 16, the fluid can be withdrawn, pumped, or otherwise removed from the inflatable member 16 and flowed back into the fluid source 22 through the inflation conduit 12 or the conduit 11, for example. After a sufficient amount of the fluid, or substantially all of the fluid, is withdrawn from the inflatable member 16, the surgical device 10, comprising the inflation conduit 12, the helical element 14, the tapered element 15, the inflatable member 16, the conduit 11, and the protective sleeve 18, can be withdrawn from the working channel 28 of the endoscope 26. Withdrawal of the surgical device 10 from the working channel 28 allows other surgical instruments or devices to be inserted into the working channel 28 and extended from the distal end of the working channel 28 to obtain access to the surgical site through the opening 34 in the tissue 32. It will be appreciated that endoscopes may comprise more than one working channel. Accordingly, other surgical instruments may be inserted through any of these additional working channels enabling the surgical device 10 to remain in-situ, for example, during a surgical procedure.

As illustrated in FIG. 16, this expansion can continue until the opening 34 is large enough to accommodate the distal end 30 of the overtube 24 and/or the distal end of the endoscope 26 therethrough, for example. Once the inflatable member 16 is inflated it fills the inside diameter of the distal end of the overtube 24, making it substantially contiguous with the overtube 24. The inflated inflatable member 16 acts as a tip for leading in and pushing the entire overtube 24 and endoscope 26 assembly through the opening 34 formed in the tissue 32 (e.g., stomach or other hollow organ wall). Once the opening 34 is expanded to a suitable size by the inflatable member 16, the fluid can be withdrawn, pumped, or otherwise removed from the inflatable member 16 and flowed back into the fluid supply 22 through inflation conduit 15 or the conduit 12. After a sufficient amount of the fluid, or substantially all of the fluid, is withdrawn from the inflatable member 16, the surgical access device 10, comprising the conduit 12, the needle 14, the inflatable member 16, the inflation conduit 15, and the protective sleeve 18, can be withdrawn from the working channel 28 of the endoscope 26. Withdrawal of the surgical access device 10 from the working channel 28 allows other surgical instruments or devices to be inserted into the working channel 28 and extended from the distal end of the working channel 28 to obtain access to the surgical site through the opening 34 in the tissue 32. It will be appreciated that endoscopes may comprise more than one working channel. Accordingly, other surgical instruments may be inserted through any of these additional working channels enabling the surgical access device 10 to remain in-situ, for example, during a surgical procedure. It will be appreciated that the overtube 24 can remain inserted through the opening 34 and the endoscope 26 withdrawn such that other instruments can be advanced through the overtube 24 to the surgical site.

In various embodiments, the overtube 24 can generally be flexible so as to allow navigation through the tortuous pathway of a body lumen during an endoscopic procedure. The size of the overtube 24 can vary but, in various embodiments, it can have a length that allows it to be inserted translumenally through a patient’s esophagus and an inner diameter or perimeter suitable to receive the endoscope 26 therein. The overtube 24 can be made flexible using various techniques. For example, the overtube 24 can be formed from a flexible material and/or it can include one or more features formed therein to facilitate flexibility, such as a plurality of cut-outs or slots, for example. In other embodiments, the overtube 24 can be formed from a plurality of linkages that are movably coupled to one another. The overtube 24 can also include regions that vary in flexibility. For example, certain portions of the overtube 24, such as the distal portion, can be more rigid than other portions of the overtube 24, such as the proximal portion, to correspond to the shape of a body lumen through which the overtube 24 is being inserted. This can be achieved by forming the overtube 24 from different materials, varying the diameter or thickness of the overtube 24, and/or using various other suitable techniques known to those of ordinary skill in the art. A person skilled in the art will appreciate that the overtube 24 can have virtually any configuration that allows the overtube 24 to flex as it is inserted through a tortuous body lumen. The overtube 24 can also include other features to facilitate use, such as one or more spiral wires embedded therein in a configuration to prevent kinking of the overtube 24 during flexure, for example. In various embodiments, the protective sleeve 18, the inflation conduit 12, and/or the conduit 11 may include any suitable features discussed above with respect to the overtube 24, for example.

The surgical device 10 as described herein can have many uses. A non-limiting example of one particular use is described below with reference to FIGS. 17 and 18. In various embodiments, a flexible endoscopic portion 131 of an endoscope 160 (e.g., gastroscope) is inserted into an upper gastrointestinal tract of a patient. FIG. 17 illustrates the surgical device 10 inserted through a natural orifice such as the mouth 110 and esophagus 112 into the stomach 114 to establish an opening in the stomach 114 for performing a surgical operation such as a gall bladder removal or a cholecystectomy, for example. FIG. 18 illustrates a distal portion 132 of the endoscope 160. As shown in FIGS. 17 and 18, the endoscope 160 may comprise the distal portion 132 and a proximal portion 140. In at least one embodiment, an overtube 130, configured to receive at least the endoscopic portion 131 of the endoscope 160, can be inserted into the mouth 110 and can extend towards and/or into the stomach 114. The overtube 130 can create a working channel for insertion of the endoscopic portion 131 of the endoscope 160. In various embodiments, the overtube 130 may be fabricated from nylon or high-density polyethylene plastic, for example. In various embodiments, the endoscopic portion 131 can define various working channels 138 that extend at least from the natural orifice 110 to the surgical site. In addition, the endoscopic portion 131 may define a viewing port 136, for example. As such, the endoscope 160 may be used for viewing the surgical site within the patient's body. Various cameras and/or lighting apparatuses may be inserted into the viewing port 136 of the endoscope 160 to provide the surgeon with a view of the surgical site.

In the embodiment illustrated in FIG. 17, one of the tools, devices, or surgical instruments that can be accommodated in the working channels 138 is a hollow vacuum/air tube 150 that may be in fluid communication with a fluid source such as at least one of a vacuum source 152 and a pressurized air source 154. In one embodiment, the vacuum/air tube 150 can be sized to receive therein another surgical instrument in the form of the endoscope 160. A variety of different types of endoscopes are known and, therefore, their specific construction and operation will not be discussed in great detail herein. In various embodiments, the endoscope 160 may operably support a video camera that communicates with a video display unit 164 that can be viewed by the surgeon during the surgical procedure. In addition, the endoscope 160 may further comprise a fluid-supply lumen therethrough that is coupled to a source of water 172, saline solution, and/or any other suitable fluid and/or an air supply lumen that is coupled to a source of air 178.

In use, the surgical device 10 can be inserted into one of the working channels 138 through either working channel port 141 or 143 and then through either working channel tube 146 or 147 to working channel 138 and used to puncture, pierce, create, or incise an opening in tissue "T" proximal to the surgical site. As illustrated in FIGS. 17 and 18, a portion of the surgical device 10 can extend from the distal end of the working channel 138 to enable access to the tissue "T." In various embodiments, the surgical device 10 can function as explained herein.

In various embodiments, again referring generally to the various stages of deployment illustrated in FIGS. 12-16, a method of using the surgical device 10 is provided. First, the surgeon can insert an overtube 24 into a natural opening of a patient, such as the mouth, for example. The surgeon can then either insert a portion of the endoscope 26 into the overtube 24 or can simply insert the surgical device 10 into the overtube 24. In many instances, the surgeon may insert the portion of the endoscope 26 before inserting the surgical device 10 to allow the surgeon to view the surgical site via a viewing port of the endoscope 26. In such an instance, the surgeon can position the surgical device 10 within and at least partially through the working channel 28 of the endoscope 26. As the surgical device 10 is inserted into the working channel 28 or the overtube 24, the protective sleeve 18 can be in the first position where it at least partially covers, shields, and protects the inflatable member 16 to prevent, inhibit, or at least minimize tearing or puncturing the inflatable member 16 during insertion. Once a distal end of the surgical device 10 reaches the surgical site, the surgeon can then turn on a vacuum producing device to create negative pressure conditions or subatmospheric pressure conditions within the overtube 24. These conditions within the overtube 24 can cause a portion of the tissue 32 near the surgical access site or surgical site to be at least partially drawn into the distal end of the overtube 24 such that the portion of the tissue 32 can be punctured by the helical element 14 of the surgical device 10.

To puncture the portion of the tissue 32, the surgeon can advance the distal end of the helical element 14 into and insert it into the tissue 32 by applying a proximal-to-distal (i.e., pushing) force, in the direction indicated by arrow "A," to the proximal portion of the helical element 14. The helical element 14 is then threaded in a clockwise direction "CW" to pierce and penetrate the tissue 32 and create the opening 34. After the helical element 14 has created the opening 34 in the tissue 32, the surgeon can then advance the distal end of the inflation conduit 12 into and through the opening 34 by applying a proximal-to-distal (i.e., pushing) force, in direction "B," to the proximal portion of the inflation conduit 12. In such an embodiment, the surgeon can also apply a proximal-to-distal (i.e., pushing) force to the handle 20 or proximal portion of the protective sleeve 18 to ensure that the protective sleeve 18 remains in the first position during insertion of the distal end of the inflation conduit 12 into and at least partially through the opening 34 in the tissue 32. In other various embodiments, a portion of the protective sleeve 18 can be releasably engaged with a portion of the inflation conduit 12 or a portion of the inflation conduit 12 to prevent, inhibit, or at least minimize sliding of the protective sleeve 18 at inappropriate times during the surgical procedure. As discussed previously, by maintaining the protective sleeve 18 in the first position during insertion into the opening 34 in the tissue 32, the inflatable member 16 can be substantially protected from puncturing, tearing, and/or premature inflation under subatmospheric pressure conditions within the overtube 24. Next, the surgeon can move and/or retract the protective sleeve 18 from the first position to a second position thereby exposing the inflatable member 16 to the sidewalls 36 of the opening 34. As previously discussed, the protective sleeve 18 can be moved using the handle 20 or by pushing or pulling the proximal portion of the protective sleeve 18, for example. Also, as discussed above, this movement of the protective sleeve 18 can be accomplished through the use of other mechanical members, such as threads, for example, or through suitable automated members, for example.

Once the protective sleeve 18 has been retracted into the second position, the surgeon can then activate the fluid source 22 to begin filling the inflatable member 16 via the inflation conduit 12 or the conduit 11. Filling the inflatable member 16 can cause the opening 34 in the tissue 32 to be enlarged as the inflatable member 16 applies a force to the sidewalls 36 of the opening 34 during expansion. Once the opening 34 has been sufficiently expanded, the overtube 24 and the endoscope 26 can be pushed or advanced through the opening 34 in the tissue 32. Subsequently, the inflatable member 16 can be deflated and the surgeon can remove the surgical device 10 from the overtube 24 or working channel 28 and insert appropriate surgical instruments or devices to begin or continue a surgical procedure.

The devices disclosed herein can be designed to be disposed of after a single use, or they can be designed to be used multiple times. In either case, however, the devices can be reconditioned for reuse after at least one use. Reconditioning can include any combination of the steps of disassembly of the devices, followed by the cleaning or replacement of particular pieces, and subsequent reassembly. In particular, the devices can be disassembled, and any number of the particular pieces or parts of the devices can be selectively replaced or removed in any combination. Upon the cleaning and/or replacement of particular parts, the devices can be reassembled for subsequent use either at a reconditioning facility or by a surgical team immediately prior to a surgical procedure. Those skilled in the art will appreciate that the reconditioning of the devices can utilize a variety of techniques for disassembly, cleaning/replacement, and reassembly. The use of such techniques, and the resulting reconditioned devices, are all within the scope of the present application.

Preferably, the various embodiments described herein will be processed before surgery. First, a new or used device is obtained and, if necessary, cleaned. The device can then be sterilized. In one sterilization technique, the device is placed in a closed and sealed container, such as a plastic or TYVEK® bag. The container and device are then placed in a field of radiation that can penetrate the container, such as gamma radiation, x-rays, or high-energy electrons. The radiation kills bacteria on the device and in the container. The sterilized device can then be stored in the sterile container. The sealed container keeps the device sterile until it is opened in the medical facility. It is preferred that the device is sterilized. This can be done by any number of ways known to those skilled in the art, including beta or gamma radiation, ethylene oxide, or steam.

Although the various embodiments have been described herein in connection with certain disclosed embodiments, many modifications and variations to those embodiments may be implemented. Also, where materials are disclosed for certain components, other materials may be used. The foregoing description and following claims are intended to cover all such modifications and variations.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical device, comprising:

a guide tube having a proximal end, a distal end, and an inside diameter;

a protective sleeve having an inner diameter larger than an outer diameter of the guide tube;

a needle having a proximal end and a distal end, the needle comprising:

a longitudinal portion having a diameter suitable to be slidably received within the inside diameter of the guide tube; and a helical element comprising a tube or a wire formed into a helical shape disposed at the distal end of the needle, wherein a distal end of the helical element is suitable for piercing tissue, and wherein a tip of the distal end of the helical element is configured to pierce the tissue through rotation of the helical element in a direction perpendicular to the longitudinal portion; and a tapered element located distally relative to the longitudinal portion and proximally relative to the helical element, the tapered element having a diameter less than the diameter of the longitudinal portion and a diameter of the tube or the wire of the helical element, the tapered element being configured to extend beyond the distal end of the guide tube and being configured to collapse by drawing, in a direction parallel to the longitudinal portion, the longitudinal portion closer to the helical element, when a force parallel to the longitudinal portion of the needle is applied to the proximal end of the needle during piercing of the tissue, the collapse of the tapered element to prevent a build up of pressure against the tissue by the needle, wherein the tapered element is shorter relative to the longitudinal portion;

wherein the protective sleeve is able to be positioned at least partially over the helical element.

2. The surgical device of claim 1, wherein the tapered element comprises:

a first tapered segment;

a second tapered segment; and a middle segment located between the first and second tapered segments, the middle segment having a diameter which is less than any one of the diameter of the longitudinal portion and the diameter of the tube or wire of the helical element.

3. The surgical device of claim 2, wherein the first tapered segment reduces the diameter of the longitudinal portion of the needle to a reduced diameter of the middle segment;

and wherein the second tapered segment reduces the diameter of the tube or the wire of the helical element to the reduced diameter of the middle segment.

4. The surgical device of claim 3, wherein the diameter of the longitudinal portion of the needle is substantially the same as the diameter of the tube or the wire of the helical element.

5. The surgical device of claim 3, wherein the diameter of the longitudinal portion of the needle is different from the diameter of the tube or the wire of the helical element.

6. The surgical device of claim 1, wherein the helical element is formed of a shape memory alloy.

7. The surgical device of claim 1, wherein the helical element is integrally formed with the longitudinal portion of the needle.

8. The surgical device of claim 1, wherein the helical element is rotatable by rotating the distal end of the needle.

9. The surgical device of claim 1, comprising a conduit to slidably receive the guide tube.

10. The surgical device of claim 1, further comprising:

a conduit having an inner diameter larger than the outer diameter of the guide tube;

an inflatable member at least partially surrounding a portion of the conduit and positioned proximal to the distal end of the guide tube, the inflatable member comprising an outer perimeter; and an inflation conduit having an inner diameter and being attached to a proximal portion of the inflatable member; and wherein the inner diameter of the protective sleeve is larger than an outer diameter of the conduit; and wherein the inner diameter of the protective sleeve is larger than an outer diameter of the inflation conduit; and wherein the inner diameter of the inflation conduit is larger than the outer diameter of the conduit.

11. The surgical device of claim 10, wherein the protective sleeve is moveable at least between a first position and a second position, the protective sleeve configured to shield the inflatable member when the sleeve is in the first position, and the protective sleeve configured to expose the inflatable member for inflation when the sleeve is in the second position.

12. A surgical device, comprising:

a guide tube having a proximal end and a distal end;

a protective sleeve having an inner diameter larger than an outer diameter of the guide tube;

an inflatable member at least partially surrounding a portion of the guide tube and positioned proximal to the distal end of the guide tube, the inflatable member comprising an outer perimeter;

a needle having a proximal end and a distal end, wherein the proximal end of the needle is attached to the distal end of the guide tube;

a helical element comprising a tube or a wire formed into a helical shape disposed at the distal end of the needle, wherein the helical element is configured to pierce tissue through rotation of the helical element; and wherein the protective sleeve surrounds at least a portion of the guide tube and is able to be positioned at least partially over the helical element, the protective sleeve moveable at least between a first position outside an incision of the tissue created by piercing of the tissue by the helical element and a second position at least partially inside the incision of the tissue, the protective sleeve configured to:

shield the inflatable member throughout the protective sleeve moving from the first position to the second position, wherein the inflatable member is positioned at least partially inside the incision of the tissue at the second position; and expose the inflatable member for inflation by moving from the second position to the first position, the inflatable member remaining at the second position; and wherein the inflatable member is configured to inflate while at least partially inside the incision of the tissue at the second position.

13. The surgical device of claim 12, further comprising a tapered element located distal to the guide tube and proximally relative to the helical element, the tapered element having a diameter less than the outer diameter of the guide tube and a diameter of the tube or wire of the helical element, wherein the tapered element is shorter relative to the guide tube; and wherein the tapered element comprises:

a first tapered segment;

a second tapered segment; and a middle segment located between the first and second tapered segments, the middle segment having a diameter which is less than any one of the outer diameter of the guide tube and the diameter of the tube or wire of the helical element.

14. The surgical device of claim 13, wherein the first tapered segment reduces the outer diameter of the guide tube to a reduced diameter of the middle segment, and wherein the second tapered segment reduces the diameter of the tube or the wire of the helical element to the reduced diameter of the middle segment.

15. The surgical device of claim 14, wherein the outer diameter of the guide tube is substantially the same as the diameter of the tube or the wire of the helical element.

16. The surgical device of claim 14, wherein the outer diameter of the guide tube is different from the diameter of the tube or the wire of the helical element.

17. The surgical device of claim 12, wherein the helical element is formed of a shape memory alloy.

18. A surgical device, comprising:

a guide tube comprising a proximal end and a distal end;

a conduit having an inner diameter larger than an outer diameter of the guide tube;

an inflatable member at least partially surrounding a portion of the conduit and positioned proximal to the distal end of the guide tube, the inflatable member comprising an outer perimeter;

a sleeve at least partially surrounding a portion of the guide tube, the sleeve comprising an elongate channel comprising an inner diameter larger than the outer diameter of the guide tube and larger than an outer diameter of the conduit; and a needle configured to be slidably disposed within the guide tube located distally relative to the inflatable member, the needle comprising:

a longitudinal portion slidably disposed within an inside diameter of the guide tube;

a helical element comprising a tube or a wire formed into a helical shape disposed at a distal end of the needle, wherein a tip of a distal end of the helical element is suitable for piercing tissue, and wherein the helical element is configured to pierce the tissue through rotation of the helical element; and a tapered element located distally relative to the longitudinal portion and proximally relative to the helical element; wherein the tapered element comprises:

a first tapered segment;

a second tapered segment; and a middle segment located between the first and second tapered segments, the middle segment having a diameter which is less than a diameter of any one of the longitudinal portion of the needle and the helical element, wherein the tapered element is shorter relative to the longitudinal portion;

wherein the sleeve is moveable at least between a first position outside an incision of the tissue created by piercing of the tissue by the helical element and a second position at least partially inside the incision of the tissue, the sleeve configured to:

shield the inflatable member throughout the sleeve moving from the first position to the second position, wherein the inflatable member is positioned at least partially inside the incision of the tissue at the second position; and expose the inflatable member for inflation by moving from the second position to the first position, the inflatable member remaining at the second position; and wherein the inflatable member is configured to inflate while at least partially inside the incision of the tissue at the second position.

19. The surgical device of claim 18, wherein the sleeve is further configured to cover the inflatable member when the sleeve is in the first position to at least inhibit the inflatable member from inflating under subatmospheric pressure conditions.

* * * * *